(12) United States Patent
Gandy et al.

(10) Patent No.: US 8,898,106 B2
(45) Date of Patent: Nov. 25, 2014

(54) METHOD FOR ENTERING, RECORDING, DISTRIBUTING AND REPORTING DATA

(75) Inventors: Woodrow W. Gandy, Dallas, TX (US);
Robert W. Langdon, Dallas, TX (US);
Scott A. Stoll, Plano, TX (US); James E. Slagle, Dallas, TX (US)

(73) Assignee: T-System, Inc., Dallas, TX (US)

( * ) Notice: Subject to any disclaimer, the term of this patent is extended or adjusted under 35 U.S.C. 154(b) by 1352 days.

(21) Appl. No.: 09/927,972

(22) Filed: Aug. 10, 2001

(65) Prior Publication Data

US 2003/0028368 A1     Feb. 6, 2003

Related U.S. Application Data

(60) Provisional application No. 60/309,452, filed on Aug. 1, 2001.

(51) Int. Cl.
*G06F 7/00*        (2006.01)
*G06F 19/00*     (2011.01)

(52) U.S. Cl.
CPC .......... *G06F 19/3487* (2013.01); *G06F 19/322* (2013.01); *G06F 19/324* (2013.01)
USPC .......................................... 707/603; 707/608

(58) Field of Classification Search
CPC ................ Y10S 707/99934; Y10S 707/99939; G06F 17/30873; G06F 9/4443; G06F 17/309991; G06F 19/325; G06F 19/326; G06Q 50/22
USPC .............. 707/1–104.1, 603, 608, 1–101, 100; 706/924, 941, 945, 779; 128/920, 922, 128/923; 340/539.12; 725/32–33, 44–53, 725/58–59

See application file for complete search history.

(56) References Cited

U.S. PATENT DOCUMENTS

| | | | |
|---|---|---|---|
| 4,829,423 A * | 5/1989 | Tennant et al. | 704/8 |
| 4,969,096 A * | 11/1990 | Rosen et al. | 434/112 |
| 5,033,812 A | 7/1991 | Yoshida et al. | |
| 5,101,459 A | 3/1992 | Sunagawa | |
| 5,132,843 A | 7/1992 | Aoyama et al. | |
| 5,436,991 A | 7/1995 | Sunagawa et al. | |
| 5,594,806 A | 1/1997 | Colbert | |
| 5,608,898 A * | 3/1997 | Turpin et al. | 707/201 |
| 5,659,640 A | 8/1997 | Joyner | |
| 5,721,938 A * | 2/1998 | Stuckey | 704/4 |
| 5,742,433 A | 4/1998 | Shiono et al. | |
| 5,787,186 A | 7/1998 | Schroeder | |
| 5,807,256 A * | 9/1998 | Taguchi et al. | 600/425 |
| 5,871,019 A * | 2/1999 | Belohlavek | 600/450 |
| 5,924,074 A * | 7/1999 | Evans | 705/3 |
| 5,956,711 A | 9/1999 | Sullivan et al. | |
| 5,991,429 A | 11/1999 | Coffin | |
| 5,995,077 A * | 11/1999 | Wilcox et al. | 715/841 |
| 6,026,363 A * | 2/2000 | Shepard | 705/3 |
| 6,040,821 A | 3/2000 | Franz et al. | |
| 6,072,894 A | 6/2000 | Payne | |
| 6,108,665 A | 8/2000 | Bair et al. | |
| 6,111,517 A | 8/2000 | Atick et al. | |
| 6,119,096 A | 9/2000 | Mann et al. | |

(Continued)

*Primary Examiner* — James Trujillo
*Assistant Examiner* — Linh Black
(74) *Attorney, Agent, or Firm* — Fulbright & Jaworski LLP

(57) ABSTRACT

An improved method for efficiently and accurately entering detailed data by yes/no entries so that the data is automatically recorded, optionally automatically distributed and optionally transformed into a readable prose report of the data, which is entered by yes/no markings.

23 Claims, 36 Drawing Sheets

(56) References Cited

U.S. PATENT DOCUMENTS

| | | | |
|---|---|---|---|
| 6,139,494 A * | 10/2000 | Cairnes | 600/300 |
| 6,151,581 A * | 11/2000 | Kraftson et al. | 705/3 |
| 6,154,726 A * | 11/2000 | Rensimer et al. | 705/2 |
| 6,184,926 B1 | 2/2001 | Khosravi et al. | |
| 6,199,034 B1 | 3/2001 | Wical | |
| 6,208,974 B1 * | 3/2001 | Campbell et al. | 705/3 |
| 6,285,813 B1 | 9/2001 | Schultz et al. | |
| 6,384,815 B1 * | 5/2002 | Huang | 345/179 |
| 6,524,241 B2 * | 2/2003 | Iliff | 600/300 |
| 6,556,977 B1 * | 4/2003 | Lapointe et al. | 706/15 |
| 6,609,091 B1 * | 8/2003 | Budzinski | 704/9 |
| 6,788,847 B2 | 9/2004 | Paddon et al. | |
| 6,871,140 B1 * | 3/2005 | Florance et al. | 701/207 |
| 7,593,952 B2 * | 9/2009 | Soll et al. | 1/1 |
| 2001/0023419 A1 * | 9/2001 | Lapointe et al. | 706/15 |
| 2001/0029322 A1 * | 10/2001 | Iliff | 600/300 |
| 2001/0037219 A1 * | 11/2001 | Malik | 705/2 |
| 2001/0041991 A1 | 11/2001 | Segal et al. | |
| 2001/0045963 A1 * | 11/2001 | Marcos et al. | 345/765 |
| 2002/0002502 A1 * | 1/2002 | Maes et al. | 705/26 |
| 2002/0004729 A1 * | 1/2002 | Zak et al. | 705/3 |
| 2002/0010679 A1 * | 1/2002 | Felsher | 705/51 |
| 2002/0016718 A1 * | 2/2002 | Rothschild et al. | 705/2 |
| 2002/0029157 A1 * | 3/2002 | Marchosky | 705/3 |
| 2002/0050982 A1 * | 5/2002 | Ericson | 345/173 |
| 2002/0082868 A1 * | 6/2002 | Pories et al. | 705/3 |
| 2002/0128816 A1 * | 9/2002 | Haug et al. | 704/4 |
| 2002/0170565 A1 * | 11/2002 | Walker et al. | 128/920 |
| 2003/0004983 A1 | 1/2003 | Cohen | |
| 2003/0055679 A1 * | 3/2003 | Soll et al. | 705/2 |
| 2003/0058277 A1 | 3/2003 | Bowman-Amuah | |
| 2003/0068134 A1 | 4/2003 | Gunn | |
| 2003/0191627 A1 | 10/2003 | Au | |
| 2004/0003142 A1 * | 1/2004 | Yokota et al. | 710/1 |
| 2004/0054630 A1 | 3/2004 | Ginter et al. | |
| 2004/0172295 A1 * | 9/2004 | Dahlin et al. | 705/2 |

\* cited by examiner

FIG. 3

T-Chart — User rlangdon

Grace | File | Edit | View | Setup

My Patients

| Room | Age | Sex | Chief Complaint | Name | Time | Template | Physician |
|------|-----|-----|-----------------|-------|------------------|-----------|-----------|
| 7    | 63y | F   | car drove off cliff | Grace | 11:26 04/12/01 | 17 MVA   | langdon   |
| 12   | 18m | M   | bean in nose    | Ricky | 15:44 04/12/01 | 28 Nose  | langdon   |

Patients Waiting

| Room | Age  | Sex | Chief Complaint      | Name        | Time            | Template | Physician |
|------|------|-----|----------------------|-------------|-----------------|----------|-----------|
|      |      |     | NEW COMPLAINT        | NEW PATIENT |                 |          |           |
|      | 49y  | F   | horse stepped on foot| Ethyl       | 16:37 04/12/01  |          |           |
|      | 118y | F   | headache             | Mary        | 16:26 04/12/01  |          |           |
|      | 56y  | M   | car crash            | Ernie       | 16:18 04/12/01  |          |           |
|      | 29y  | M   | abdominal pain       | Jack        | 15:26 04/12/01  |          |           |
|      | 37y  | M   | chest pain           | Desi        | 15:04 04/12/01  |          |           |

Side panel:
- Home
- Annotations
- Notes
- Clinical
- History
- Exam
- Clinical Course
- DxD1
- Viewing
- Report
- Discharge
- Prescription
- Excuse
- Printing
- Clinical
- Discharge
- Closure

FIG. 4

| T-Chart | | | | | | | | | |
|---|---|---|---|---|---|---|---|---|---|
| Grace | User rlangdon | | | | | | | | _ 🗗 ☒ |
| 🏠 Home | File Edit View Setup 💾🖨 ⬜ ⬜ ⬜ 🔍 🔧 📁 📅 🕐 ⬜ 🔍 | | | | | | | | |
| Annotations | My Patients | | | | | | | | |
| ✏️ | Room | Age | Sex | Chief Complaint | | Name | Time | Template | Physician |
| 📝 Notes | 7 | 63y | F | car drove off cliff | | Grace | 11:26 04/12/01 | 17 MVA | langdon |
| Clinical | 12 | 18m | M | bean in nose | | Ricky | 15:44 04/12/01 | 28 Nose | langdon |
| 👁 History | | | | | | | | | |
| 🔍 Exam | | | | | | | | | |
| 📋 Course | | | | | | | | | |
| 💡 DxDl | | | | | | | | | |
| Viewing | Patients Waiting | | | | | | | | |
| Report | Room | Age | Sex | Chief Complaint | | Name | Time | Template | Physician |
| Discharge | | | | NEW COMPLAINT | | NEW PATIENT | | | |
| Prescription | | 49y | F | horse stepped on foot | | Ethyl | 16:37 04/12/01 | | |
| Kxcuse | | 118y | F | headache | | Mary | 16:26 04/12/01 | | |
| Printing | | 56y | M | car crash | | Ernie | 16:18 04/12/01 | | |
| 🩺 Clinical | | 37y | M | chest pain | | Desi | 15:04 04/12/01 | | |
| 🚪 Discharge | | 29y | M | abdominal pain ← | | Jack | 04/12/01 3 2 | | |
| Closure | | | | | | | | | |
| 🔒 🚪 | | | | | | | | | |

FIG. 5

T-Chart — User rlangdon

File  Edit  View  Setup

Jack  🏠 Home

My Patients

| Room | Age | Sex | Chief Complaint | Name | Time | Template | Physician |
|------|-----|-----|-----------------|------|------|----------|-----------|
|      | 29y | M   | abdominal pain  | Jack | 15:26 04/12/01 |  | langdon |
| 7    | 63y | F   | car drove off cliff | Grace | 11:26 04/12/01 | 17 MVA | langdon |
| 12   | 18m | M   | bean in nose    | Ricky | 15:44 04/12/01 | 28 Nose | langdon |

Patients Waiting

| Room | Age | Sex | Chief Complaint | Name | Time | Template | Physician |
|------|-----|-----|-----------------|------|------|----------|-----------|
|      |     |     | NEW COMPLAINT   | NEW PATIENT |  |  |  |
|      | 49y | F   | horse stepped on foot | Ethyl | 16:37 04/12/01 |  |  |
|      | 118y | F  | headache        | Mary | 16:26 04/12/01 |  |  |
|      | 56y | M   | car crash       | Ernie | 16:18 04/12/01 |  |  |
|      | 37y | M   | chest pain      | Desi | 15:04 04/12/01 |  |  |

Annotations
 ✏
 🗒 Notes
Clinical
 📖 History
 🔍 Exam
 ⏱ Course
 ☤ DxDI
Viewing
 Report
 Discharge
 Prescription
 Excuse
 Printing
 🖨 Clinical
 🖨 Discharge
Closure

FIG. 6

User rlangdon

File  Edit  View  Setup

My Patients

| Room | Age | Sex | Chief Complaint | Name | Time | | Template | Physician |
|------|-----|-----|-----------------|------|------|------|----------|-----------|
| 7 | 63y | F | car drove off cliff | Grace | 11:26 | 04/12/01 | 17 MVA | langdon |
| 8 | 29y | M | abdominal pain | Jack | 15:26 | 04/12/01 | | langdon |
| 12 | 18m | M | bean in nose | Ricky | 15:44 | 04/12/01 | 28 Nose | langdon |

Patients Waiting

| Room | Age | Sex | Chief Complaint | Name | Time | | Template | Physician |
|------|-----|-----|-----------------|------|------|------|----------|-----------|
| | | | NEW COMPLAINT | NEW PATIENT | | | | |
| | 49y | F | horse stepped on foot | Ethyl | 16:37 | 04/12/01 | | |
| | 118y | F | headache | Mary | 16:26 | 04/12/01 | | |
| | 56y | M | car crash | Ernie | 16:18 | 04/12/01 | | |
| | 37y | M | chest pain | Desi | 15:04 | 04/12/01 | | |

Jack · Home · Annotations · Notes · Clinical · History · Exam · Course · DxDl · Viewing · Report · Discharge · Prescription · Excuse · Printing · Clinical · Discharge · Closure

FIG. 7

| T-Chart Template Selector | |
|---|---|
| Trauma | Medicine |
| 1 Head Injury | 26 Headache |
| 2 Eye Problems | 27 Ear Complaints |
| 3 head Injury, Facial | 28 Nose |
| 4 Neck/Back Pain or Injury | 29 Throat or Dental Pain |
| 5 Shoulder Injury | 30 Cough |
| 6 Upper Extremity Injury | 31 Wheezing/Asthma |
| 7 Trunk Injury | 32 Dyspnea |
| 8 Low Back Pain or Injury | 33 Chest Pain |
| 9 Hand/Wrist Injury | 34 Palpitations |
| 10 Hip Injury | 35 Upper Extremity Pain |
| 11 Lower Extremity Injury | 36 Abdominal Pain |
| 12 Ankle/Foot Injury | 37 Vomiting/Diarrhea |
| 13 Plantar Puncture Wound | 38 GI bleeding/Rectal Pain |
| 14 Pediatric Illness | 39 Female GU |
| 15 Asthma-pediatric | 40 OB Problems |
| 16 Pediatric trauma | 41 Male GU |
| 17 MVA | 42 Lower Extremity Pain |
| 17a MCA Bike/Pedestrian | 43 Skin Rash/Abscess |
| 18 Multiple trauma | 44 Allergy |
| 19 Fall | 45 Changed Mental Status |
| 20 Assault | 46 Focal Neuro Deficit |
| 21 Animal Bite | 47 Dizzy |
| 22 Major Burn/Smoke Inhalation | 48 Syncope |
| 23 Recheck/Suture Removal | 49 Seizure |
| 24 General | 50 CPR |
| | 51 Critical Care |
| | 52 Overdose |
| | 53 Psych |

Ok  Cancel

FIG. 8

| T-Chart Template Selector | |
|---|---|
| Trauma | Medicine |
| 1 Head Injury | 26 Headache |
| 2 Eye Problems | 27 Ear Complaints |
| 3 head Injury, Facial | 28 Nose |
| 4 Neck/Back Pain or Injury | 29 Throat or Dental Pain |
| 5 Shoulder Injury | 30 Cough |
| 6 Upper Extremity Injury | 31 Wheezing/Asthma |
| 7 Trunk Injury | 32 Dyspnea |
| 8 Low Back Pain or Injury | 33 Chest Pain |
| 9 Hand/Wrist Injury | 34 Palpitations |
| 10 Hip Injury | 35 Upper Extremity Pain |
| 11 Lower Extremity Injury | 36 Abdominal Pain |
| 12 Ankle/Foot Injury | 37 Vomiting/Diarrhea |
| 13 Plantar Puncture Wound | 38 GI bleeding/Rectal Pain |
| 14 Pediatric Illness | 39 Female GU |
| 15 Asthma-pediatric | 40 OB Problems |
| 16 Pediatric trauma | 41 Male GU |
| 17 MVA | 42 Lower Extremity Pain |
| 17a MCA Bike/Pedestrian | 43 Skin Rash/Abscess |
| 18 Multiple trauma | 44 Allergy |
| 19 Fall | 45 Changed Mental Status |
| 20 Assault | 46 Focal Neuro Deficit |
| 21 Animal Bite | 47 Dizzy |
| 22 Major Burn/Smoke Inhalation | 48 Syncope |
| 23 Recheck/Suture Removal | 49 Seizure |
| 24 General | 50 CPR |
|  | 51 Critical Care |
|  | 52 Overdose |
|  | 53 Psych |

Ok  Cancel

FIG. 9B

_similar symptoms previously:
  once twice sev. times many times - occasionally frequently
  milder as bad worse varying _recently seen
  ED office clinic hospitalized

| Closure |
|---|
| 🔒 📋 |

(A)→

0 MEDS  _none  _see nurses notes _____

0 ALLERGIES  _NKDA  _see nurses notes _____

0 SOCIAL Hx  smoker _____  ETOH _____  drugs _____
residence/travel:

0 FAMILY Hx  gall bladder _____  heart dz _____  hx of: _____ 0

FIG. 10

| T-Chart | Abdominal Pain | time: _____ | room: _____ |
|---|---|---|---|
| Jack | arrived: pvt vehicle EMS | | context: |
| 🏠 Home | historian: patient EMS family _____ | | limited by: _____ |
| Annotations | ○HPI | | |
| ✎ | chief complaint: abdominal pain _____ flank pain | | |
| 📝 Notes | started: just PTA today↖last night yesterday | | |
| Clinical | still present _____ gone _____ timing: _____ | | |
| 📖 History | quality, location: R chest _central_L chest | | |
| | "pain" epig | | |
| | sharp | | |

○ROS
GI
  _vomiting blood
  _black stools
  _bloody stools
URINARY
  _difficulty w/urination
  _pain w/urination
  _frequency
  Female _pregnant
  LNMP CONSTITUTIONAL
  _fever _chills
Neuro & EENT
  _headache
  _sore throat
  _blurred vision
CVS & Pulmonary
  _chest pain
  _difficulty breathing
  _cough

| T-Chart | Abdominal Pain | time: ___ | room: ___ | context: ___ |
| Jack | arrived: pvt vehicle  EMS |  |  | limited by: ___ |
|  | historian: patient  EMS  family |  |  |  |

□ Home
Annotations ✎ ⌘
☐ Notes
Clinical
📖 History
⟳ Exam
Q Course
Q DxDI
Viewing
Report
Discharge
Prescription
Excuse
Printing
⬅ Clinical
⬅ Discharge

OHPI
chief complaint: (abdominal pain) ___ flank pain ___
started: just PTA  today  last night  yesterday ___
still present ___ gone ___ timing: ___
quality      location:  R chest _ central_ L chest
"pain"                        epig
sharp                   RUQ upper LUQ               L flank
stabbing                    generalized
cramping                        o
burning                  RLQ      LLQ
dull                 R pelvis pelvis L pelvis
migrating                    suprapub
                R flank                              L back
...
well localized
diffuse         R back ___ additional pain ___
_radiating to: ___
associated symptoms: ___ vomiting ___
(nausea) _ loss of appetite ___ diarrhea ___
severity of pain: ___
modifying factors: ___

OROS
GI
_vomiting blood ___
_black stools ___
_bloody stools ___
URINARY
_difficulty w/urination ___
_pain w/urination ___
_frequency ___
_Female _ pregnant ___
LNMP
_missed periods _ irreg ___
_abdominal bleeding ___
_all systems neg. except as marked

CONSTITUTIONAL
_fever _ chills
Neuro & EENT
_headache
_sore throat
_blurred vision
CVS & Pulmonary
_chest pain
_difficulty breathing
_cough
MS & Skin
_joint pain _ back pain
_skin rash

OPAST Hx
_negative _ see nurses notes      _heart diz      _neuro diz
_peptic ulcer                      _lung diz       _GI diz
_gall stones                       _renal dz       _other dz
_bowel obstruction                 _HTN            _diabetes
_kidney stones                     _hyperlipidemia
                                   _previous surgery
                                   _abdominal surgery

FIG. 13

| T-Chart | Abdominal Pain | time: | room: | |
|---|---|---|---|---|
| Jack | arrived: pvt vehicle EMS | | context: | |
| | historian: patient EMS family | | limited by: | |

○HPI chief complaint: (abdominal pain) flank pain
started: just PTA today last night yesterday still present ___ gone ___ timing: ___ location:  R chest  central  L chest      flank pain
                              epig
                    RUQ  upper  LUQ
                              generalized        L flank
                    RLQ          LLQ
                R pelvis pelvis L pelvis
                         suprapub
        R flank                              L back
                    R back        additional pain quality
 "pain"
 sharp
 stabbing
 cramping
 burning
 dull
 migrating
...
 well localized
 diffuse
 _radiating to: ___
associated symptoms:  ___ vomiting
 (nausea)           ___ diarrhea
 (loss of appetite)
 severity of pain:
 modifying factors:

○ROS

GI
 _vomiting blood
 _black stools
 _bloody stools
URINARY
 _difficulty w/urination
 _pain w/urination
 _frequency
 _Female _pregnant
LNMP
 _missed periods _irreg
 _abdominal bleeding
 _all systems neg, except as marked CONSTITUTIONAL
 _fever _chills
Neuro & EENT
 _headache
 _sore throat
 _blurred vision
CVS & Pulmonary
 _chest pain
 _difficulty breathing
 _cough
MS & Skin
 _joint pain _back pain
 _skin rash

○PAST Hx

_negative  _see nurses notes
_peptic ulcer
_gall stones
_bowel obstruction
_kidney stones _heart diz  _neuro diz
_lung diz   _GI diz
_renal dz   _other dz
_HTN        _diabetes
_hyperlipidemia
_previous surgery
_abdominal surgery Sidebar:
- Home
- Annotations
- Notes
- Clinical
- History
- Exam
- Course
- DxDl
- Viewing
- Report
- Discharge
- Prescription
- Excuse
- Printing
- Clinical
- Discharge

FIG. 14

| T-Chart | Abdominal Pain | time: | room: | | oROS |
|---|---|---|---|---|---|

Jack
arrived: pvt vehicle EMS context:
historian: patient EMS family limited by:

Home

Annotations

Notes

Clinical

History

Exam

Course

DxDI

Viewing

Report

Discharge

Prescription

Excuse

Printing

Clinical

Discharge oHPI
chief complaint: (abdominal pain) ___ flank pain ___
started: just PTA today last night yesterday ___ still present ___ gone ___ timing: ___
quality: ___ location: ___ R chest _central_ L chest ___ L flank
"pain" ___ epig ___
sharp ___ RUQ upper LUQ ___
stabbing ___ R flank generalized
cramping ___ 0
burning ___ RLQ LLQ
dull ___ R pelvis pelvis L pelvis
migrating ___ suprapub
... ___ < ___
well localized ___ R back ___ L back
diffuse ___
_radiating to: ___ _additional pain ___
associated symptoms: ___ _vomiting ___
(nausea) (loss of appetite) ___ _diarrhea ___
severity of pain: ___
modifying factors: ___

GI
_vomiting blood ___
_black stools ___
_bloody stools ___
URINARY
_difficulty w/urination ___
_pain w/urination ___
_frequency ___
Female _pregnant ___
LNMP
_missed periods _irreg ___
_abdominal bleeding ___
_all systems neg. except as marked CONSTITUTIONAL
_fever _chills
Neuro & EENT
_headache
_sore throat
_blurred vision
CVS & Pulmonary
_chest pain
_difficulty breathing
_cough
MS & Skin
_joint pain _back pain
_skin rash oPAST Hx
_negative _see nurses notes
_peptic ulcer
_gall stones
_bowel obstruction
_kidney stones _heart diz _neuro diz
_lung diz _GI diz
_renal dz _other dz
_HTN _diabetes
_hyperlipidemia
_previous surgery
_abdominal surgery

FIG. 15

| T-Chart | Abdominal Pain | time: _____ room: _____ |
|---|---|---|
| Jack | arrived: pvt vehicle EMS | context: _____ |
|  | historian: patient EMS family | limited by: _____ |

○HPI
chief complaint: (abdominal pain) _____ flank pain _____
started: just PTA today last night yesterday _____
still present _____ gone _____ timing: _____
quality, location: R chest _central _L chest
"pain" epig
sharp RUQ upper LUQ
stabbing generalized L flank
cramping
burning RLQ LLQ
dull R pelvis pelvis L pelvis
migrating suprapub
... ∧
well localized
diffuse R back L back
_radiating to: _____ additional pain _____
associated symptoms: _vomiting_
(nausea) _diarrhea_
(loss of appetite)
severity of pain: _____
modifying factors: _____

○ROS
GI
_vomiting blood _____
_black stools _____
_bloody stools _____
URINARY
_difficulty w/urination _____
_pain w/urination _____
_frequency _____
_Female _pregnant _____
LNMP _____
_missed periods _irreg _____
_abdominal bleeding _____
_all systems neg. except as marked CONSTITUTIONAL
_fever _chills _____
Neuro & EENT
_headache _____
_sore throat _____
_blurred vision _____
CVS & Pulmonary
_chest pain _____
_difficulty breathing _____
_cough _____
MS & Skin
_joint pain _back pain _____
_skin rash _____

○PAST Hx
_negative _see nurses notes
_peptic ulcer
_gall stones
_bowel obstruction
_kidney stones _heart diz _neuro diz
_lung diz _GI diz
_renal dz _other dz
_HTN _diabetes
_hyperlipidemia
_previous surgery
_abdominal surgery Sidebar:
Home
Annotations
Notes
Clinical
History
Exam
Course
DxD1
Viewing
Report
Discharge
Prescription
Excuse
Printing
Clinical
Discharge

FIG. 16

Clinical Report
Hospital Name-
Emergency Department
Street Address - 214-555-1212
12-Apr-2001

Patient Name: Jack

HISTORY OF PRESENT ILLNESS
Chief complaint- ABDOMINAL PAIN. He has had nausea and loss of appetite. No vomiting or diarrhea.

_____
Physician Signature

T-Chart | Jack | Home | Annotations | Notes | Clinical History | Exam | Course | DxD1 | Viewing | Report | Discharge | Prescription | Excuse | Printing | Clinical | Discharge | Closure

FIG. 17

| T-Chart | Abdominal Pain | time: | room: |
|---|---|---|---|
| Jack | arrived: pvt vehicle EMS | | context: |
| | historian: patient EMS family | | limited by: |

OHPI
chief complaint: (abdominal pain) ___ flank pain ___
started: just PTA today last night yesterday ___ still present ___ gone ___ timing: ___
location: R chest _central_ L chest
                      epig
              RUQ upper LUQ        L flank
   R flank      generalized
                      o
               RIQ    LLQ
             R pelvis pelvis L pelvis
                   suprapub
   R back                              L back quality
 "pain"
 sharp
 stabbing
 cramping
 burning
 dull
 migrating ...  well localized
     diffuse                  ___ additional pain ___ radiating to: ___
associated symptoms:       ___ vomiting
  (nausea)                 ___ diarrhea
  (loss of appetite)
severity of pain:
modifying factors:

OROS

GI
___ vomiting blood
___ black stools
___ bloody stools
URINARY
___ difficulty w/urination
___ pain w/urination
___ frequency
Female ___ pregnant
LNMP
___ missed periods ___ irreg
___ abdominal bleeding
___ all systems neg. except as marked CONSTITUTIONAL
___ fever ___ chills
Neuro & EENT
___ headache
___ sore throat
___ blurred vision
CVS & Pulmonary
___ chest pain
___ difficulty breathing
___ cough
MS & Skin
___ joint pain ___ back pain
___ skin rash

OPAST Hx
___ negative ___ see nurses notes
___ peptic ulcer
___ gall stones
___ bowel obstruction
___ kidney stones ___ heart diz    ___ neuro diz
___ lung diz    ___ GI diz
___ renal dz    ___ other dz
___ HTN         ___ diabetes
___ hyperlipidemia
___ previous surgery
___ abdominal surgery Annotations
Notes
Clinical
History
Exam
Course
DxDl
Viewing
Report
Discharge
Prescription
Excuse
Printing
Clinical
Discharge
Home

[T-Chart | Abdominal Pain  time:____  room:____
Jack    arrived: pvt vehicle  EMS____  context:____
        historian: patient  EMS  family____  limited by:____
○HPI
chief complaint: (abdominal pain)____ flank pain____
started: just PTA  today  last night  yesterday
still present____ gone____ timing:____
quality  location:  R chest_central_L chest
"pain"              epig
sharp              RUQ upper LUQ
stabbing              generalized
cramping       R flank                    L flank
burning              o
dull                RLQ    LLQ
migrating          R pelvis pelvis L pelvis
                    suprapub
well localized      ^
diffuse       R back                      L back
radiating to:____  ____additional pain
associated symptoms:____ —vomiting
  (nausea)                —diarrhea
  -(loss of appetite)
severity of pain:____
modifying factors:____

○ROS
GI
_vomiting blood          CONSTITUTIONAL
_black stools            _fever _chills
_bloody stools           Neuro & EENT
URINARY                  _headache
_difficulty w/urination  _sore throat
_pain w/urination        _blurred vision
_frequency               CVS & Pulmonary
_Female _pregnant        _chest pain
LNMP                     _difficulty breathing
_missed periods          (cough)
_abdominal blee
_all systems neg. e minutes       (<<)
                              hours
○PAST Hx                      days         ago
_negative _see nur   1 2 3 4 5   weeks    times
_peptic ulcer      for 6 7 8 9 0 1/2  months
_gall stones          several    years
_bowel obstruction    many
_kidney stones        occasionally
                   today  since yesterday  recently  chronically
                   -gone now  -still present  -improving  -worsening COUGH
                mild  moderate (severe)
....
dry / (productive)
scant  moderate  copious (thick) thin
clear  yellow (green) brown  white
(blood tinged) frank blood ← smoker
cough changed from baseline
sputum changed from baseline
....
similar to previous symptoms]

Home
Annotations
Notes
Clinical
History
Exam
Course
DxDl
Viewing
Report
Discharge
Prescription
Excuse
Printing
Clinical
Discharge

FIG. 20

Clinical Report
Hospital Name-
Emergency Department
Street Address - 214-555-1212
12-Apr-2001

Patient Name: Jack

HISTORY OF PRESENT ILLNESS
Chief complaint- ABDOMINAL PAIN. He has had nausea and loss of appetite. No vomiting or diarrhea.

REVIEW OF SYSTEMS
The patient has had a sever cough productive of thick, green, blood tinged sputum. No frankly bloody sputum.

_____
Physician Signature

Sidebar buttons:
- T-Chart Jack
- Home
- Annotations
- Notes
- Clinical
- History
- Exam
- Course
- DxDl
- Viewing Report
- Discharge Prescription
- Excuse Printing
- Clinical
- Discharge
- Closure

| T-Chart | Abdominal Pain | time: | room: |
|---|---|---|---|
| Jack | arrived: pvt vehicle EMS | | context: |
| | historian: patient EMS family | | limited by: |

OHPI
chief complaint: (abdominal pain) flank pain
started: just PTA today last night yesterday
still present gone timing:
quality,           location: R chest _central _L chest
 "pain"                       epig
 sharp                  RUQ upper LUQ      L flank
 stabbing                 generalized
 cramping                        o
 burning              RLQ    LLQ
 dull                R pelvis pelvis L pelvis
 migrating              suprapub
                                          L back
 well localized   R flank
 diffuse           R back      additional pain
radiating to: _____
associated symptoms: vomiting
 nausea    diarrhea
 (loss of appetite)
severity of pain:
modifying factors:

oROS
GI
 _vomiting blood
 _black stools
 _bloody stools
URINARY
 _difficulty w/urination
 _pain w/urination
 _frequency
 Female _pregnant
 LNMP
 _missed periods _irreg
 _abdominal bleeding
 _all systems neg. except as marked CONSTITUTIONAL
 _fever _chills
Neuro & EENT
 _headache
 _sore throat
 _blurred vision
CVS & Pulmonary
 _chest pain
 _difficulty breathing
 (cough) severe,productive,thick gr
MS & Skin
 _joint pain _back pain
 _skin rash oPAST Hx
 _negative _see nurses notes      _heart dz    _neuro dz
 _peptic ulcer                    _lung dz     _GI dz
 _gall stones                     _renal dz    _other dz
 _bowel obstruction               _HTN         _diabetes
 _kidney stones                   _hyperlipidemia
                                  _previous surgery
                                  _abdominal surgery

- Home
- Annotations
- Notes
- Clinical
- History
- Exam
- Course
- DxDI
- Viewing
- Report
- Discharge
- Prescription
- Excuse
- Printing
- Clinical
- Discharge

| T-Chart | RESPIRATORY | _resp distress |
| Jim | _chest nontender | _chest wall injury #1 _____ #2 |
| 🏠 Home | _breath snds nml | _decreased breath sounds |
| Annotations | | _rales _____ rhonchi |
| ✏️ | | _wheezes _____ crepitus |
| 📝 Notes | CVS | _abnml rate techycardia bradycardia |
| Clinical | _heart snds nml | _abnml rhythm |
| 🩺 History | _pulses nml | _JVD present |
| 🔍 Exam | | _extra sounds _____ murmur |
| I Course | | _pulse exam |
| 💊 DxDl | ABDOMEN | _obese _____ scar _____ other |
| Viewing | _soft | _tenderness _____ #1 _____ #2 |
| Report | _nontender | _guarding |
| Discharge | _no organomegaly | _rebound |
| Prescription | | _organomegaly _____ gravid uterus |
| Excuse | | _abnml bowel sounds |
| Printing | | _distention |
| 🖨️ Clinical | | _mass |
| 📄 Discharge | GU | _panneal hematoma |
| | _nml genitalia | _blood at urethral meatus |
| | _nml vaginal exam | |
| | RECTAL | _blood in stool |
| | _nml rectal exam | _abnormal digital rectal |
| | _heme neg stool | |
| | BACK | _tenderness _____ #2 |
| | _nontender | _vertebral point tenderness |
| Closure | _ROM nml | _muscle spasm _____ limited ROM |
| 🔒 🔓 | | |

O NEURO _____ _altered mental status _____ GCS
_oriented x3 _____ _CN deficit
_no motor deficit _____ _weakness _____ sensory deficit
_no sensory deficit _____ _reflex exam:
_reflexes nml SKIN _____ _cyanosis _____ pallor
_intact _____ _cool skin _____ diaphoresis
_warm, dry _____ _skin rash _____ poor skin turgor
_nml color EXTREMITIES _____ _soft tissue tenderness
_atraumatic _____ _bony tenderness
_nml inspection _____ _abrasions _____ #1 _____ #2
_pelvis stable _____ _limping gait _____ cannot bear weight
_no pedal edema _____ _gait not tested due to pain shoulder          shoulder          LT
                         clavicle | clavicle
                    arm    chest    arm
              elbow       abdomen      elbow
         forearm            ○  back     forearm
            wrist  hip  GU  hip   wrist
     RT      hand   thigh  thigh    hand
                    knee            knee
                    leg              leg
            ankle  ○              ○  ankle
                    foot            foot

| T-Chart | CLINICAL IMPRESSION | PRESCRIPTIONS |
|---|---|---|
| Jim | acute pain _____ MVA MCA bike pedestrian _____ | OTC meds _____ NSAID's _____ antibiotics _____ |
| Home | skin _____ fracture _____ | OTC meds _____ Ibuprofen _____ Augmentin _____ |
| Annotations | laceration _____ skull _____ rib _____ | Acetaminophen _____ Lodine _____ Cephalexin _____ |
| ✎ 🖉 | abrasion(s) _____ facial _____ pelvic _____ | Motrin _____ Naproxen _____ Cipro 10d _____ |
|  | skin avulsion _____ spine _____ hip _____ |  Duricef _____ |
| Notes | foreign body, soft tissue _____ upper ext _____ lower ext _____ | pain / nausea _____ muscle _____ Erythromycin _____ |
|  | soft tissue _____ wrist _____ ankle _____ | Darvocet-N _____ Flexeril _____ Levaquin _____ |
| Clinical | cervical strain _____ hand _____ foot _____ | Lortab _____ Robaxin _____ Silvadene _____ |
| History | neck pain _____ other / major injury _____ | Phenergan _____ Skelaxin _____ |
|  | back pain _____ concussion _____ | Tylenol w/Cod. _____ Soma _____ |
| Exam | strain _____ head injury _____ | more prescriptions _____ |
|  | sprain _____ spinal injury _____ | o Allergy/Decong o Eye o Nsaids o Sedative |
| Course | contusion _____ hemorrhage _____ | o Analgesics o ENT o M.Relax o Skin |
|  | dislocation _____ hypotension _____ | o Antibiotics o GI o Ob-Gyn o Steroids |
| DxDI | shoulder _____ finger _____ shock _____ | o Cardiac o Neuro o Pulmonary o Urology |
| Viewing | elbow _____ toe _____ respiratory failure _____ | o DISCHARGE INSTRUCTIONS |
| Report | knee injury _____ chest injury _____ | treatment _____ o activity / work-school |
|  | knee injury _____ cardiac arrest _____ | c-collar _____ no restrictions _____ |
| Discharge | hemarthrosis _____ abdominal injury _____ | ice _____ no strenuous activity _____ |
| Prescription | knee instability _____ renal injury _____ | wound care _____ elevate _____ wt bearing as tolerated _____ |
| Excuse |  dental trauma _____ | sling _____ splint _____ no wt bearing _____ |
|  | abnormal test _____ general _____ | rib belt _____ RT work _____ off work _____ |
| Printing | lifestyle issues _____ hypertension _____ | crutches _____ RT school _____ off school _____ |
|  |  diabetes _____ | knee immobilizer _____ warnings _____ |
| Clinical |  more diagnoses _____ | elastic wrap _____ head _____ comps _____ |
| Discharge |  |  diet _____ infection _____ Tet given _____ |
|  | o Allergy o Infectious Disease o Ortho/Surg | no restrictions _____ sedative meds in ED _____ |
|  | o Cardiology o Int Medicine, Gen 1 o Pediatrics | clear liquids only _____ return if problems _____ |
|  | o Dermatology o Mouth/Dental o Psychiatric |  |
|  | o ENT o Eye o Pulmonary o Toxocology | follow-up _____ |
| Closure | o Environmental o Neurology o Trauma | o _w/ Dr. _____ w/ your doctor _____ |
| 🏠 🖨 | o Gastrointestinal o OB-GYN o Urology | o _w/ Dr. (#2) _____ w/ specialist _____ |
|  |  | return to ED _____ discharged home in _____ |

| | | |
|---|---|---|
| EVI | nurses notes rev'd __ VS rev'd __ O 2/other __ | |
| Mary | | |
| 🏠 Home | PHYSICAL EXAM | |
| Annotations | _alert _anxious / lethargic / obtunded | |
| ✏️ | _NAD _in distress mild mod severe | |
| 📝 Notes | EYES _conjunctival findings | ABDOMEN _(obese)_ _scar_ _other_ |
| Clinical | _nml inspection _(scleral icterus) | _soft _tenderness _#1 _#2 |
| 📖 History | _PERRL _(pale conjunctivae) | _nontender _(guarding)_ |
| 🔍 Exam | ENT _abnml ear exam | _no organomegaly _(rebound)_ _organomegaly _gravid uterus |
| 💬 Course | _(ears nml) _runny nose | _abnml bowel sounds |
| ❓ DxDl | _nose nml _pharyngeal erythema | _distention |
| Viewing | _pharynx nml _tonsillar exudate | _mass |
| Report | _dry mucous membranes | O FEM GENITALIA _vag. bleeding __ discharge |
| Discharge | NECK _JVD | _external exam nml _bimanual tenderness |
| Prescription | _nml inspection _cartoid bruit | _bimanual exam nml _enlarged uterus __ mass |
| Excuse | _supple _(lymphadenopathy) | _speculum exam nml |
| Printing | _(thyromegaly) | MALE GENITALIA _tenderness |
| 🩺 Clinical | _(meningeal signs) | _nml genitalia _scrotal swelling |
| 🩺 Discharge | CVS _abnml rate _tachycardia _bradycardia | _testes descended |
| | _nml rate/rhythm _abnml rhythm | RECTAL _blood in stool |
| | _heart sounds nml _murmur | _nml rectal exam _tenderness |
| | _extra sounds | _nontender _abnormal digital rectal |
| | _decrsd pulses | _hemo neg stool |
| | RESPIRATORY _resp distress | BACK _CVA tenderness |
| | _no resp distress _accessory muscles | _nml inspection |
| | _breath sounds nml _decreased air movement | EXTREMITIES _pedal edema |
| | _chest nontender _rales | _nml ROM _calf tenderness |
| | | _no pedal edema |
| | | SKIN _(cyanosis)_ _pallor |
| | | _nml color _cool skin _diaphoresis |

↱(B)

*FIG. 28B* rhonchi
wheezes
prolonged expirations warm, dry
no rash
0 NEURO
oriented x
no motor deficit
no sensory deficit
reflexes nml skin rash    poor skin turgor
altered mental status
CN deficit
weakness
sensory deficit
reflex exam:

Closure

*FIG. 29*

Clinical Report
Hospital Name -- Emergency Department
Street Address - 214-555-1212
12-Apr-2001

Patient Name: Mary

PHYSICAL EXAM
Eyes: Scleral icterus. Pale conjunctivae.
ENT: Ears normal. Nasal discharge present. Dry mucous membranes present.
Neck: Meningeal signs present. Lymphadenopathy present. Thyromegaly.
Abdomen: Obese. Rebound tenderness. Guarding present.
Skin: Cyanosis. Skin rash.
Neuro: Oriented X 3. No motor deficit. No sensory deficit.

_____
Physician Signature

FIG. 30

PHYSICAL EXAM nurses notes rev'd ___ VS rev'd ___ O2/other ___ ABDOMEN ___ (obese) scar ___ other
_alert _anx _in d ___ soft ___ tenderness #1 ___ #2
_NAD gyn ⊠

EYES _conj ___ PELVIC EXAM
_nml inspection _scle (speculum) (bimanual) rectovag
_PERRL _pale _external exam nml _herpes-like lesion(s) ___ egaly ___ gravid uterus
 _speculum exam nml _vaginal discharge ___ owel sounds
ENT _abn _no vag discharge _vag. bleeding ___ n
_ears nml _run _IUD string visible ___ ding ___ discharge
_nose nml _pha _no cervical lesions _cervical erosion ___ tenderness
_pharynx nml _tons _os closed _cervicitis ___ uterus
 _dry (cervical lesion)
NECK _JVD (cervical discharge) ___ ss
_nml inspection _cart _cervical dilation ___ welling
_supple (lym) _cervical os open
 _thyr _tissue in os in vagina ___ stool
CVS _men _cerv. effacement ___ ss
_nml rate/rhythm _abnm _bimanual exam nml _cerv. motion tenderness ___ digital rectal
_heart sounds nml _abn _nontender bimanual _bimanual tenderness
 _mur _no pelvic mass _pelvic mass ___ erness
 _extr _adnexal tenderness
RESPIRATORY _decr _adnexal mass / fullness ___ ema
_no resp distress _resp _retroverted uterus ___ erness
_breath sounds nml _acce _retroflexed uterus
_chest nontender _decr RECTAL _uterine tenderness _pallor
 _rale _nml rectal exam _enlarged uterus _diaphoresis
 _heme neg stool _decreased rectal tone
 _nontender _blood in stool
 _abnormal digital rectal

FIG. 31

Clinical Report
Hospital Name–
Emergency Department
Street Address – 214-555-1212
26-Jul-2001

Patient Name: Jane

PAST HISTORY
Peptic ulcer, Gall stones, Bowel obstruction

PHYSICAL EXAM
Eyes: Schleral icterus. Pale conjunctivae.
ENT: Ears normal. Nasal discharge persent. Dry mucous membranes present.
Neck: Meningeal signs present. Lymphadenopathy present. Thyromegaly.
Abdomen: Obese. Rebound tenderness. Guarding present.
GU: Speculum and bimanual exam performed. Cervical lesion present.
Discharge present from the cervical os.
Skin: Cyanosis. Skin rash.
Neuro: Oriented X 3. No motor deficit. No sensory deficit.

_____
Physician Signature

T-Chart Jane
- Home
- Annotations
- Notes
- Clinical
- History
- Exam
- Course
- DxDI
- Viewing
- Report
- Discharge
- Prescription
- Excuse
- Printing
- Clinical
- Discharge
- Closure

FIG. 32

| T-Chart | EKG / XRAYS / STUDIES | | PROCEDURE NOTES | |
|---|---|---|---|---|
| Jane | O EKG _nml | O CT Head _NAD | O Intubation | O Central Line |
| Home | O CXR _NAD | O CT Chest _NAD | O Ventilator Management | O Thrombolytic Therapy |
| Annotations | O V/Q scan _nml | O CT Abdomen _NAD | O Chest tube | |
| | O Abdomen _NAD | O Abdominal Sono _NAD | PROGRESS | |
| Notes | O IVP _NAD | O Pelvic Sono _NAD | | |
| | O Other X-rays _neg | O Other studies _neg | | |
| Clinical | LAB | | TIME: _____ | unstable |
| History | O CBC | O Chem | AFTER: | gone (much better) better unchngd |
| Exam | nml except | CMP BMP ISTAT | reassessment | (exam improved) unchanged |
| Course | WBC ___ | nml except | multiple exams | [PPLY] |
| DxDl | Hgb ___ | Na ___ | (observation) | Physical exam findings are |
| Viewing | HCT ___ | K ___ | return to dept | |
| Report | Plat ___ | Cl ___ | (tests back) | s. Physical exam findings are |
| Discharge | segs ___ | HCO3 ___ | Evaluat ___ | ptoms are unchanged. |
| Prescription | bands ___ | Glu __#2 | unchan ___ | |
| Excuse | lymphs ___ | BUN ___ | | IV fluids |
| Printing | monos ___ | Cr ___ | Evaluat ___ | Phenergan |
| Clinical | O COAG | Tol Prol ___ | unchan ___ | MS Toradol |
| Discharge | PT ___ | Albumin ___ | | Nubain Demerol |
| Closure | PTT ___ | T.Bili ___ | O gener ___ | GI cocktail |
| | INR ___ | SGOT ___ | | |
| | | Alk Phos ___ | | meds (analgesic) |
| | TYPE / Rh | Ca ___ | _D/W ___ | antibiotx anxiolytic |
| | Time ___ | Mg ___ | _D/W ___ | antiemetic (narcotic) |
| | T & C ___ | PO4 ___ | _tried ___ | antispasmotic |
| | Type/Rh ___ | Amylase ___ | _fami ___ | CVS O CPR O re-evaluation |
| | | Lipase ___ | | review of records |
| | | | | _old records ordered |
| | | O Cardiac Enz | | _old records reviewed |
| | | nml except | | _records req-unavailable |
| | | CK ___ | | _further history sought |
| | | CKMB ___ | | |
| | | myoglobin ___ | | sion or transfer |
| | | Troponin T ___ | _adm ___ | _good condition |
| | | Troponin I ___ | _transfer ___ | _stable |
| | | O Pulse Ox | _observation status ___ | |
| | | time ___ | | |
| | | FIO2 ___ | | |
| | | O2 sat ___ | | |
| | | O ABG | | |
| | | time ___ | | |
| | | FIO2 ___ | | |
| | | pO2 ___ | | |
| | | O2 sat ___ | | |
| | | pCO2 ___ | | |
| | | pH ___ | | |
| | | O PFTs | | |
| | | Peak Flow ___ | | |
| | | O U/A | | |
| | | cath clean | | |
| | | nml except | | |
| | | WBCs ___ | | |
| | | RBCs ___ | | |
| | | bacteria ___ | | |
| | | blood ___ | | |
| | | leuk est ___ | | |
| | | nitrite ___ | | |
| | | gluc ___ | | |
| | | ketones ___ | | |
| | | Bili ___ | | |
| | | protein ___ | | |
| | | HCG ___ | | |
| | | sHCG ___ | | |
| | | Quant ___ | | |
| | | uHCG ___ | | |

FIG. 33

| T-Chart | EKG / XRAYS / STUDIES | | PROCEDURE NOTES |
|---|---|---|---|
| Jane | 0 EKG _nml | 0 CT Head _NAD | 0 Intubation            0 Central Line |
| | 0 CXR _NAD | 0 CT Chest _NAD | 0 Ventilator Management   0 Thrombolytic Therapy |
| Annotations | 0 V/Q scan _nml | 0 CT Abdomen _NAD | 0 Chest tube |
| ✎ ✂ | 0 Abdomen _NAD | 0 Abdominal Sono _NAD | PROGRESS |
| 🗐 Notes | 0 IVP _NAD | 0 Pelvic Sono _NAD | TIME: ___ - now    stable      unstable |
| | 0 Other X-rays _neg | 0 Other studies _neg | sx's gone  much better  better  unchngd |
| Clinical | LAB | | exam improved            unchanged |
| 📖 History | 0 __ CBC | 0 __ Chem | 0 __ Cardiac Enz | 0 __ PFTs | _____[APPLY]_____ |
| 🔍 Exam | nml except | CMP BMP ISTAT | nml except | Peak Flow ___ | Evaluation after reassessment. Physical exam findings are |
| 🕒 Course | | nml except | | 0 ___ U/A | unchanged. |
| ❓ DxDI | WBC ___ | Na ___ | CK ___ | cath  clean | |
| | Hgb ___ | K ___ | CKMB ___ | nml except | Evaluation after multiple exams. Physical exam findings are |
| Viewing | HCT ___ | Cl ___ | myoglobin ___ | WBCs ___ | unchanged. The patient's symptoms are unchanged. |
| Report | Plat ___ | HCO3 ___ | Troponin T ___ | RBCs ___ | |
| Discharge | segs ___ | Glu __ #2 __ | Troponin I ___ | bacteria ___ | Evaluation after observation, results of tests back, analgesic and |
| Prescription | bands ___ | BUN ___ | 0 ___ Pulse Ox | blood ___ | narcotic. Physical exam findings are improved. Symptoms much |
| Excuse | lymphs ___ | Cr ___ | ___ time ___ | leuk est ___ | better. |
| | monos ___ | Tol Prol ___ | FIO2 ___ | nitrite ___ | 0 general course   0 Resp / CVS     0 CPR    0 re-evaluation |
| Printing | 0 ___ COAG | Albumin ___ | 02 sat ___ | gluc ___ | |
| ⚕ Clinical | PT ___ | T.Bili ___ | 0 ___ ABG | ketones ___ | _____ consultation / review of records |
| 🏥 Discharge | PTT ___ | SGOT ___ | ___ time ___ | Bili ___ | ___ D/W Dr. ___          ___ old records ordered ___ |
| | INR ___ | Alk Phos ___ | FIO2 ___ | protein ___ | ___ D/W Dr.(#2) ___      ___ old records reviewed ___ |
| Closure | | Ca ___ | pO2 ___ | | ___ tried - can't contact Dr. ___  ___ records req-unavailable ___ |
| 🏠 ⚔ | TYPE / Rh ___ | Mg ___ | 02 sat ___ | HCG ___ | ___ family consultation ___     ___ further history sought ___ |
| | Time ___ | PO4 ___ | pCO2 ___ | sHCG ___ | |
| | T & C ___ | Amylase ___ | pH ___ | Quant ___ | _____ hospital admission or transfer |
| | Type/Rh ___ | Lipase ___ | | uHCG ___ | ___ admit ___                ___ good condition ___ |
| | | | | | ___ transfer ___              ___ stable ___ |
| | | | | | ___ observation status ___ |

*FIG. 34*

Clinical Report
Hospital Name-
Emergency Department
Street Address - 214-555-1212
26-Jul-2001

Patient Name: Jane

PAST HISTORY
  Peptic ulcer, Gall stones, Bowel obstruction
PHYSICAL EXAM
  Eyes: Schleral icterus. Pale conjunctivae.
  ENT: Ears normal. Nasal discharge persent. Dry mucous membranes present.
  Neck: Meningeal signs present. Lymphadenopathy present. Thyromegaly.
  Abdomen: Obese. Rebound tenderness. Guarding present.
  GU: Speculum and bimanual exam performed. Cervical lesion present. Discharge present from the cervical os.
  Skin: Cyanosis. Skin rash.
  Neuro: Oriented X 3. No motor deficit. No sensory deficit.
PROGRESS AND PROCEDURES
  E.D. Course: Evaluation after reassessment. Physical exam findings unchanged.

Evaluation after multiple exams. Physical exam findings are unchanged. The patient's symptoms are unchanged.

Evaluation after observation, results of tests back, analgesis and narcotic. Physical exam findings are improved. Symptoms much better.

_____
Physician Signature

[Sidebar tabs: T-Chart Jane, Home, Annotations, Notes, Clinical, History, Exam, Course, DxDl, Viewing Report, Discharge, Prescription, Excuse, Printing, Clinical, Discharge, Closure]

METHOD FOR ENTERING, RECORDING, DISTRIBUTING AND REPORTING DATA

RELATED APPLICATIONS

This Application is entitled to and hereby claims the benefit of the filing date of provisional application 60/309,452 filed Aug. 1, 2001, entitled "Method For Entering, Recording, Distributing and Recording Data" by Woodrow W. Gandy, Robert W. Langdon, Scott A. Stoll and James E. Slagle.

FIELD OF THE INVENTION

This invention relates to an improved method for efficiently and accurately entering detailed data by yes/no markings so that the data is automatically recorded, optionally automatically distributed and optionally transformed into a readable prose report of the data.

BACKGROUND OF THE INVENTION

Many computer systems have been proposed for entering data of a variety of types for a variety of purposes. Many of the systems rely upon relatively standardized yes/no entries but produce relatively non-informative reports. For instance, in FIG. 1 a prior art system is shown. Particularly when relatively detailed data is being taken and reported, the relatively simplified reporting system in FIG. 1 is wholly inadequate. Among the deficiencies in this type of data record is the fact that the recorder must expend a certain amount of effort to scan the yes/no columns for categories for marks and then correlate those to his findings. The recorders typically object to these seemly trivial efforts which are required to enter data on the form and it becomes clumsy and difficult to navigate when large numbers of entries must be organized and presented in such a fashion.

Accordingly, considerable effort has been directed to the development of improved systems for recording data especially in environments where considerable amounts of detailed data about a wide variety of subjects must be recorded and where the data must be recorded in some detail. One such instance is in medical emergency rooms where doctors are required to record data very quickly in order to provide a record for use by the hospital staff and to record their findings, proposed treatment, and the like with a minimum of effort. Similar situations exist in a number of other areas, but the requirements are particularly acute in hospital emergency room situations.

Previously, manual data entry systems have been used along with relatively simplistic forms such as shown in FIG. 1 on computers.

These systems have not been adequate to meet the requirements for detailed data recording.

Accordingly, an improved method has been sought which permits reporting of detailed amounts of data by yes/no entries by a physician or other recorder of information very efficiently.

SUMMARY OF THE INVENTION

According to the present invention, such data is effectively entered quickly and efficiently to produce at least one of a retrievable data base and a language text report of the entered data, by a system for entering data by yes/no entries and producing at least one of a retrievable data base and a language text report of the entered data. The system comprises: a workstation comprising a computer, including a screen capable of displaying a template form capable of receiving entries of yes/no data, capable of accessing a computer and programmed to permit access by an authorized user; a plurality of templates, each of the templates showing a plurality of relevant inquiries and capable of accepting data entry as yes/no entries by a user, said templates being accessible on the workstation or on a computer accessible by the workstation; a system access display programmed on the workstation or accessible by the workstation and providing the capability for a user to access a selected database or a selected template; a plurality of modifiers related to and associated with designated inquiries on at least a portion of the templates showing more detailed inquiries related to the inquiries on the templates for the entry of additional data; a retrievable database accessible by or on the workstation for storing and retrieving entered data from at least one of the templates and modifiers; and, a language program accessible by the workstation and capable of producing a language text report of the entered data.

The present invention further comprises a method for distributing copies of medical records the method comprising: entering medical records into a medical records database; entering a plurality of distribution options into a distribution database;

Selecting a distribution option from the distribution database; distributing medical records according to the selected distribution option; and, retaining in a database a record of the distribution of the medical records for retrieval as required.

The present invention further comprises a system for distributing copies of medical records, the system comprising: a database containing the medical records; a computer programmed to access the database and to distribute the medical records according to at least one selected distribution option via at least one communication means; and, a database programmed to retain a record of the medical records sent and the address to which the medical records were sent for retrieval upon request.

The present invention further comprises a method for generating easily readable English or other language text from simple sentences with each of the sentences reporting a single data entry and optionally containing modifiers of the data entry. The method comprises a method for generating easily readable English text from simple sentences, each of the sentences reporting a single data entry and optionally containing modifiers of one or more of the data entries comprising: selecting the words or phrases which correspond to the reported data entries; selecting which words or phrases can be combined into a single sentence and selecting the order of the selected words or phrases; limiting the number of words or phrases which can be combined in a single sentence;

arranging the words or phrases so that modifiers modify only the designated word or phrase; and, supplying the punctuation and conjuctives to create the English text.

BRIEF DESCRIPTION OF THE DRAWINGS

FIGS. 2 through 28 and 30 through 32 illustrate screen displays demonstrating the use of the present invention on a computer equipped to run the system of the present invention on a Microsoft Windows™ software program on a Microsoft Windows™ capable computer.

FIG. 29 shows a clinical report produced by the system of the present invention; and, FIGS. 33 through 37 demonstrate a program for producing reports from the system of the present invention.

DESCRIPTION OF THE PREFERRED EMBODIMENTS

In the description of the present invention, a plurality of computer screens will be shown. It will be understood that the computer screens are illustrative only and that other screens could be used with different formats to perform the same functions. The screens shown in this Description of Preferred Embodiments illustrate screen displays, which have been found particularly effective for use in the entry of data in a medical emergency room application. The system of the present invention is equally effective in other situations where data entry is required.

Figure 1:
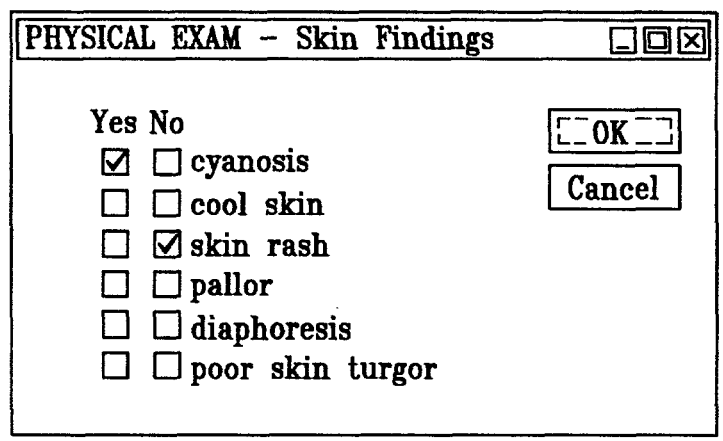
FIG. 1 shows a prior art computer display screen for yes/no data entry.
Figure 2:
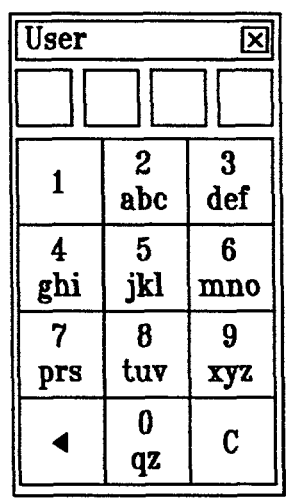

In FIG. 2 a typical security display is shown. The user is required to enter his password to provide security for access to the system.

The system comprises a computer programmed to perform the required functions. The computer can be a handheld terminal, a personal computer, a terminal accessing a suitable computer and the like. The data entry can be by a computer entry pen, by clicks on a mouse by use of a keyboard, or the like. Particularly, in emergency medical room environments a pen-friendly system may be used. After entry of the required password, the system displays a screen (system access display) as shown in FIG. 3. This is a main screen or home view of the program. The upper section headed "My Patients" shows all patients presently assigned to a physician. The lower section, "Patients Waiting," shows a list of patients about whom the program has been notified from another computer such as the hospital's admission system but for whom no medical data has yet been entered into this program.

The workstation used by the physician or other data recorder can be a handheld unit, a personal computer a computer workstation or the like. As indicated previously, the data may be entered by pen strokes, by clicking a mouse, typing on a keyboard or the like. The workstation is also programmed to access a hospital or other mainframe computers to acquire data about the patients presently assigned to the physician. Software and programming for the exchange of such information between computers is well known to those skilled in the art.

In FIG. 4, a patient named "Jack" has been selected for treatment. This patient has been identified by the pointer and in FIG. 5 has been moved to the "My Patients" section which is accomplished by dragging the patient's name from the lower to the upper section of the screen. The patient is now assigned to the attending physician. The physician may also move the new complaint from the lower to the upper section of the screen. This entry allows the physician to begin entering data for the patient who may have not been previously admitted by the hospital admitting system.

In FIG. 6, the physician has identified a patient room for the patient. The physician can also enter the patient's vital statistics, such as name, sex, age, chief complaint, arrival time, etc., using the same technique as for the room number. The system usually discourages changing information of this type, which may have been received from the hospital directly. In addition to the use of pen/tablet devices, other devices may be used which can provide handwriting recognition to support the data entry process. Voice recognition may also be used for this purpose.

With the room number assigned, the physician has a clear view of his/her current patients as shown in FIG. 6. The highlighted patient is identified as the selected patient who will be the subject of the actions described below. It will be understood that the physician could alternatively select a different patient by selecting, tapping or clicking on a different patient. Please note in FIG. 6 at the left under "Clinical" four entries are possible: "History"; "Exam"; "Course"; and "DxDI." These entries refer to different sections of the system and provide templates, which may be used to enter different types of data.

The "History" section allows the entry of data pertaining to the history of the present illness, a review of systems, a past history (including social history) and may include the first part of a physical exam, if desired. It is into this section that the physician will usually first begin entering data.

The "Exam" should allow the entry of the majority of information regarding a physical examination.

The "Course" section provides for entry of data regarding various procedures and the progress of the case during the course of the patient's visit to the emergency room or hospital departments. The physician can return to this section several times during the course of a patient's visit.

The "DxDI" provides for the entry of clinical impression, prescriptions, work excuse, discharge instructions and the like. This section is generally used by the physician to complete a case.

As indicated previously, these sections appear at the left side of the main screen and can be selected by computer entry pen strokes, by clicking a mouse, typing on a keyboard or the like. Various other operations can be selected for various other software functions from the system access display.

If the physician taps or clicks one of the sections on a selected patient and the patient currently has no current medical record, the program prompts the physician to select the desired template by displaying a template selector as shown in FIG. 7.

Each template provides for entry by the physician of the clinically relevant data for the associated chief complaint. Each template also provides for the entry of data less clinically relevant to the chief complaint. For example, the template for a motor vehicle accident should provide for entry of crucial information about head injuries, which are of a particular concern in such cases. It also should provide for the entry of somewhat detailed information about broken bones, however, it need only provide rudimentary entering capabilities for injuries such as insect bites. For this reason, the program need only allow a single template, which may be selected for a given patient visit.

As shown in FIG. 8, in the described template, "Abdominal Pain" has been selected by positioning the arrow on the desired template. Selecting the desired template results in the display of a chart as shown in FIG. 9 for abdominal pain. This illustration shows the "History" section for abdominal pain. The History section under "clinical" is as shown. The physician can easily view the other sections by selecting the "Exam", "Course" or "DxDI" buttons. Tapping or clicking the home button beneath the patient's name brings back the original view of the patients on the main screen.

In FIG. 10, a selection is indicated by the arrow that abdominal pain is or will be the chief complaint. The present system does not use conventional check boxes or other data entry methods. The current system has been developed to be readily grasped and used by physicians who are not expert computer users but still appeal to highly computer literate individuals.

It is important that the organization of the data entry points presents itself to the user in a manner that provides effortless orientation for both new and experienced users.

FIG. 10, shows a mouse cursor positioned over a finding of abdominal pain as the chief complaint in the history of present illness portion of the "History" section of a template for abdominal pain.

Figure 9A:

Please note the small circles to the left of "HPI", "ROS" and "Past Hx" in FIG. 9A. These indicate the availability of sub-templates for these headings. Sub-templates will be discussed in greater detail below.

Figure 11:
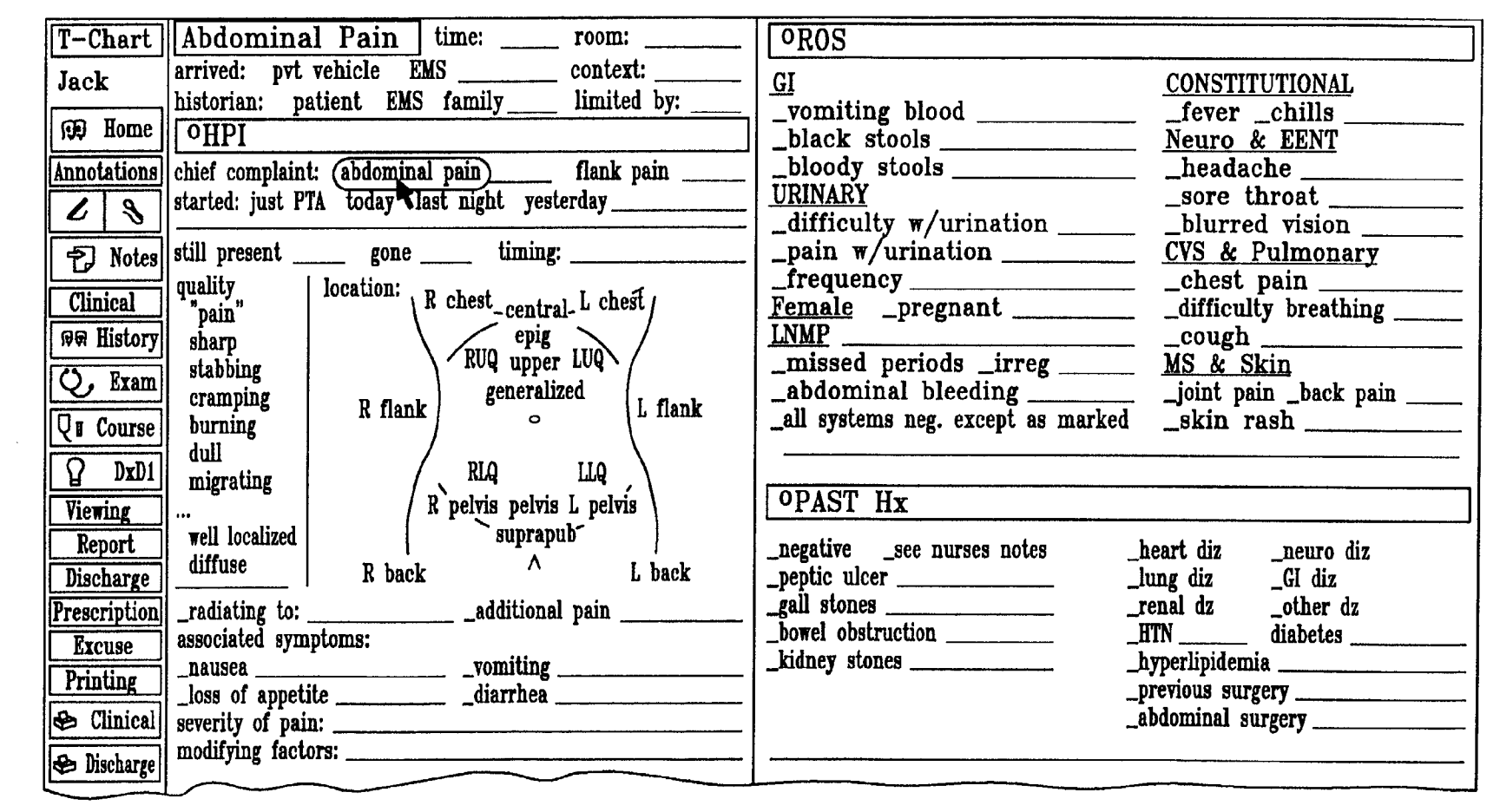

In FIG. 10, tapping or clicking the heading "abdominal pain" results in a circle around the term "abdominal pain" indicating a positive finding. As shown in FIG. 11, an indication of abdominal pain is shown. In FIG. 12 a further indication has been made that nausea is present. This indication is made in the same way by selecting "Nausea." In FIG. 13, the information has been added that there has been loss of appetite. This is done by tapping or clicking on the "Loss of Appetite" term.

In FIG. 14, it has been indicated that there is no vomiting. Using the secondary mouse button (normally the right button), or tapping with a tablet pen near the right of the word creates a backslash instead of a circle. This indicates a negative finding, in this case, no vomiting.

In FIG. 15, a further indication has been made in the same way that there is no diarrhea.

Although the circles and backslashes provide an ideal visual representation of findings, it is necessary to present this information in a text format which can be stored in hospital archives, transmitted, printed and viewed without the requirement for a graphical presentation. Clicking the report entry as shown on the main screen beneath the viewing section, causes the program to generate a textual (prose) representation of the remarks entered by the physician. In FIG. 16, the clinical report of the information entered previously is shown in textual form.

Figure 18:
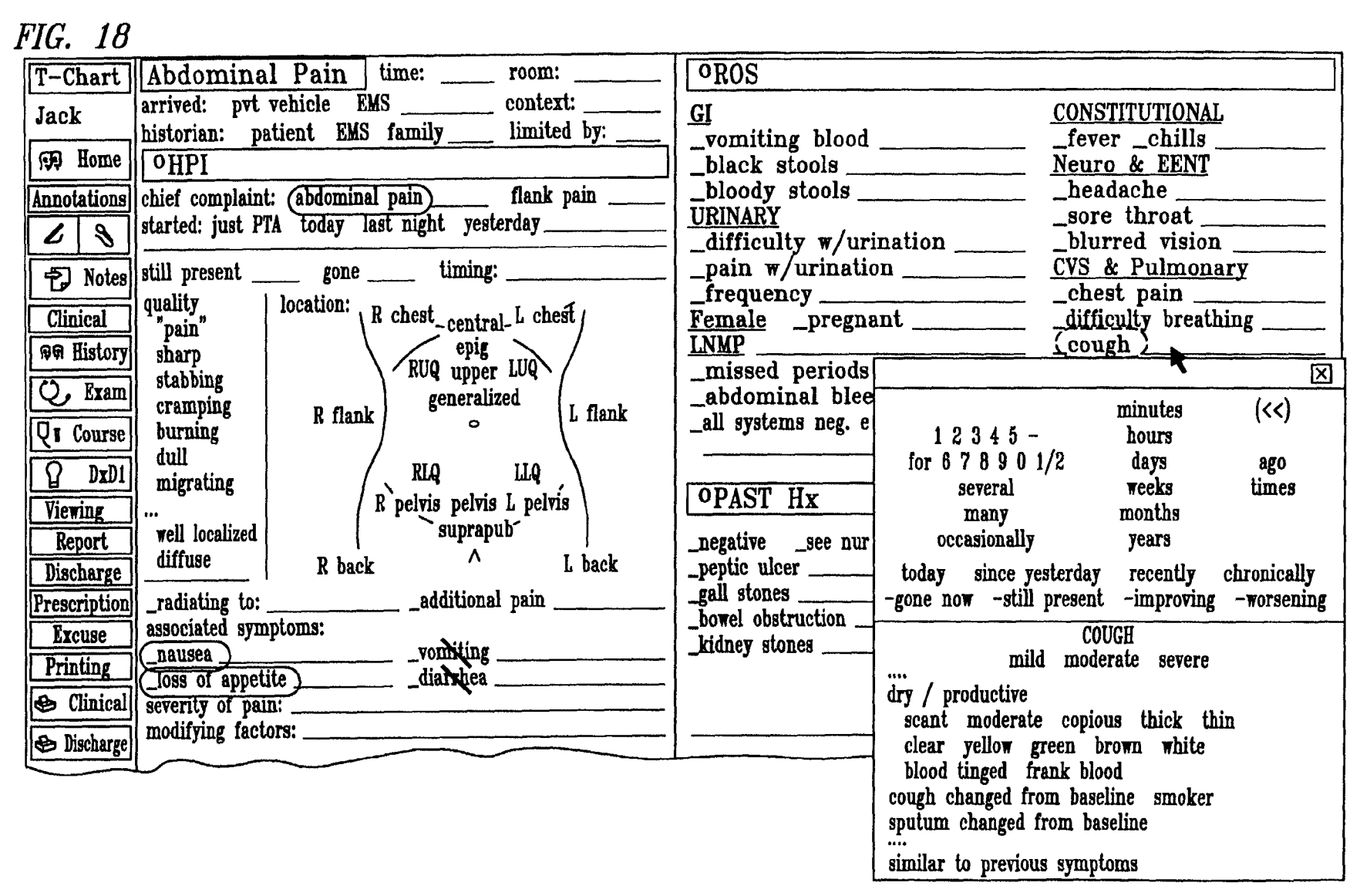

In FIG. 17, the cursor has been placed on the line at "Cough" and selecting the entry at the line may permit the entry of more detailed information. The system provides methods for going into greater detail. The mouse pointer shown over the line in FIG. 17 extending to the right of "Cough" permits clicking on the line which brings up additional details (modifier) one might wish to describe for that finding as shown in FIG. 18.

As shown in FIG. 19, the recorder has indicated on the modifier that the cough is severe, that it has been productive, thick, green and blood-tinged but with no "frank blood". These details are entered by circles and backslashes as described previously.

The clinical report based upon this additional information is shown in FIG. 20.

Figure 21:
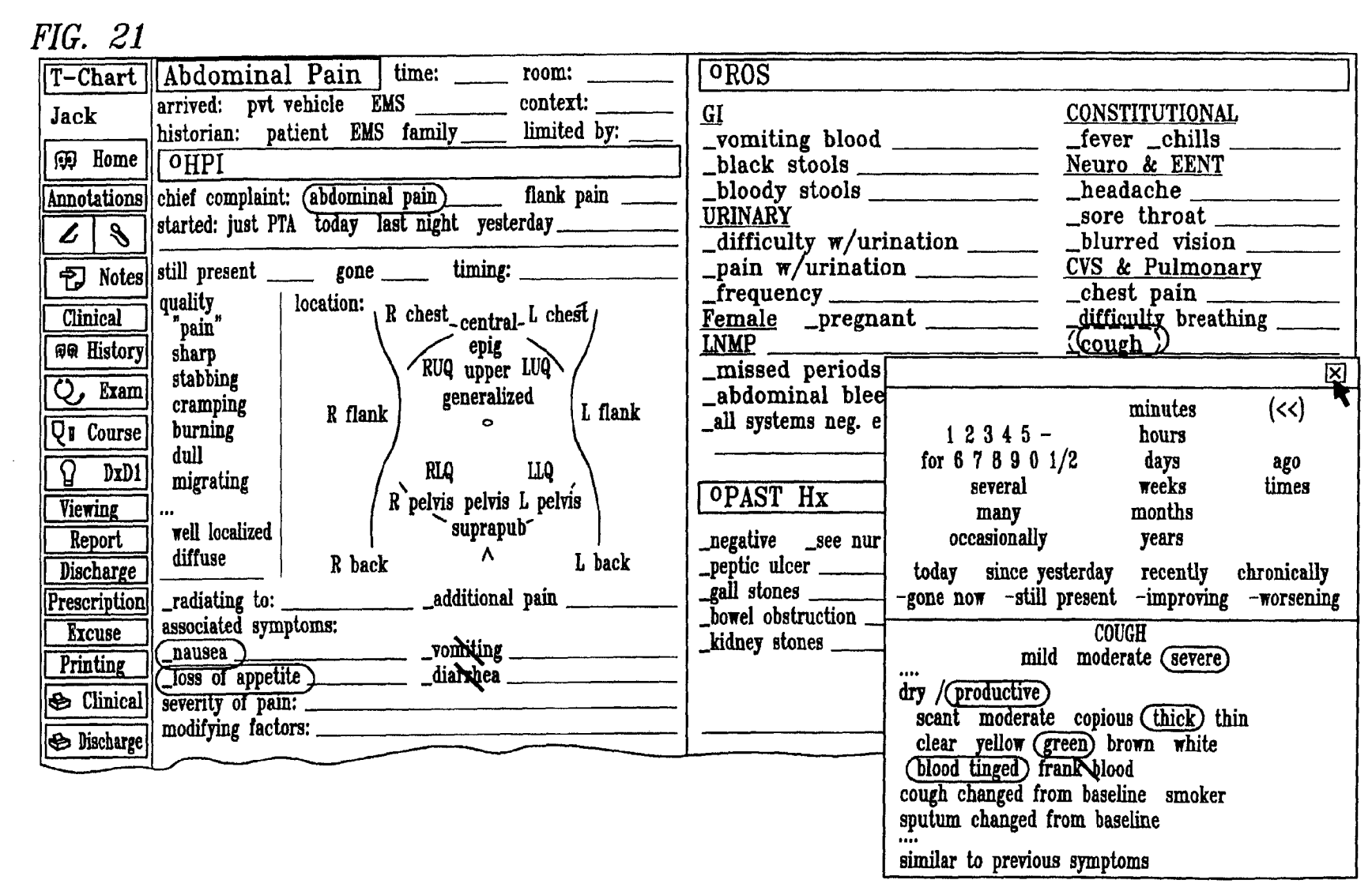

In FIG. 21, it is indicated that by clicking on the "X" at the upper right the modifier can be deleted. It can also be deleted by clicking or tapping another finding somewhere else on the screen.

After the modifier has been deleted, (FIG. 22) the additional information remains on the line following "Cough" indicating that more information is available.

Figure 23:
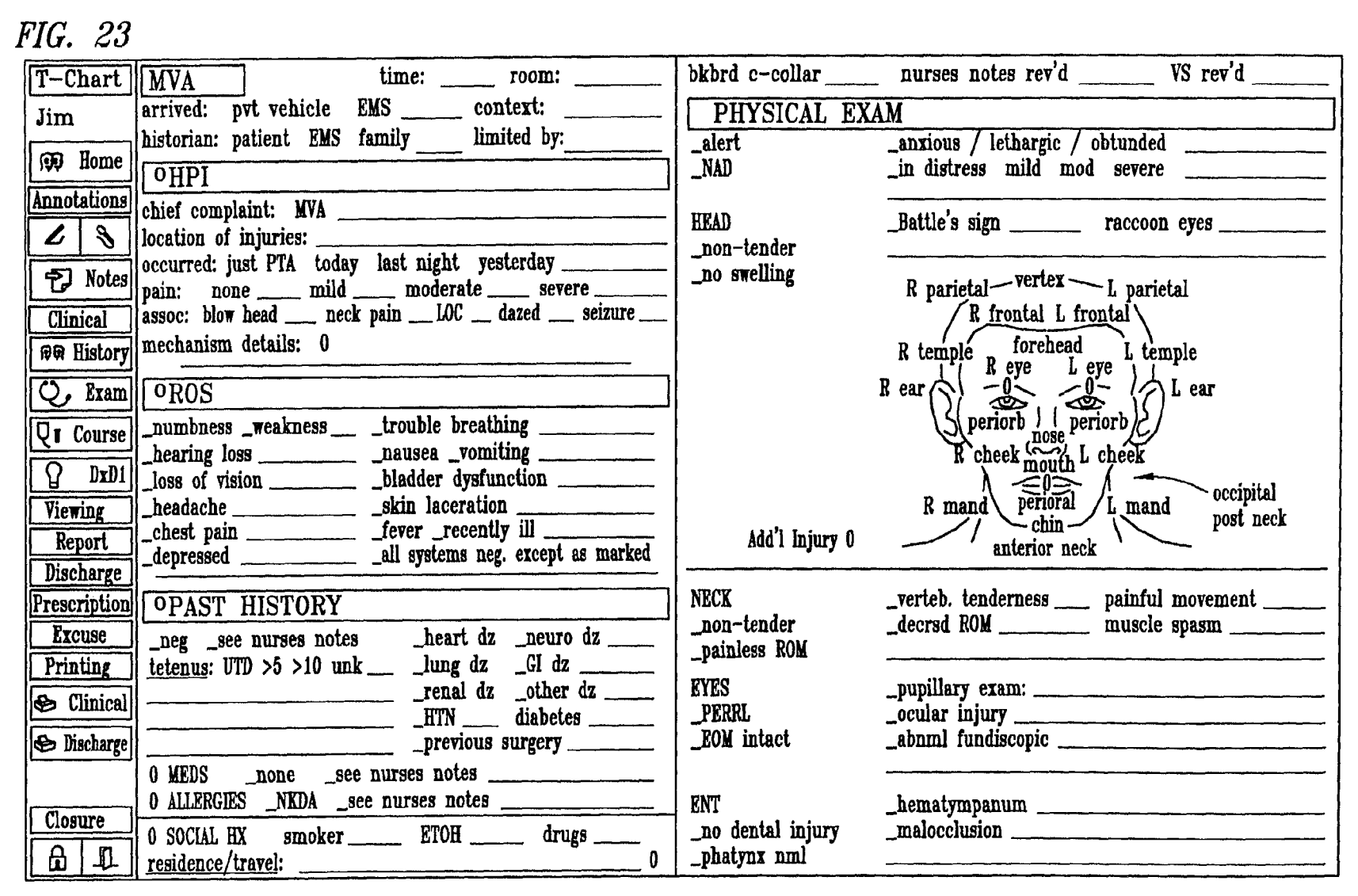
Figure 25:
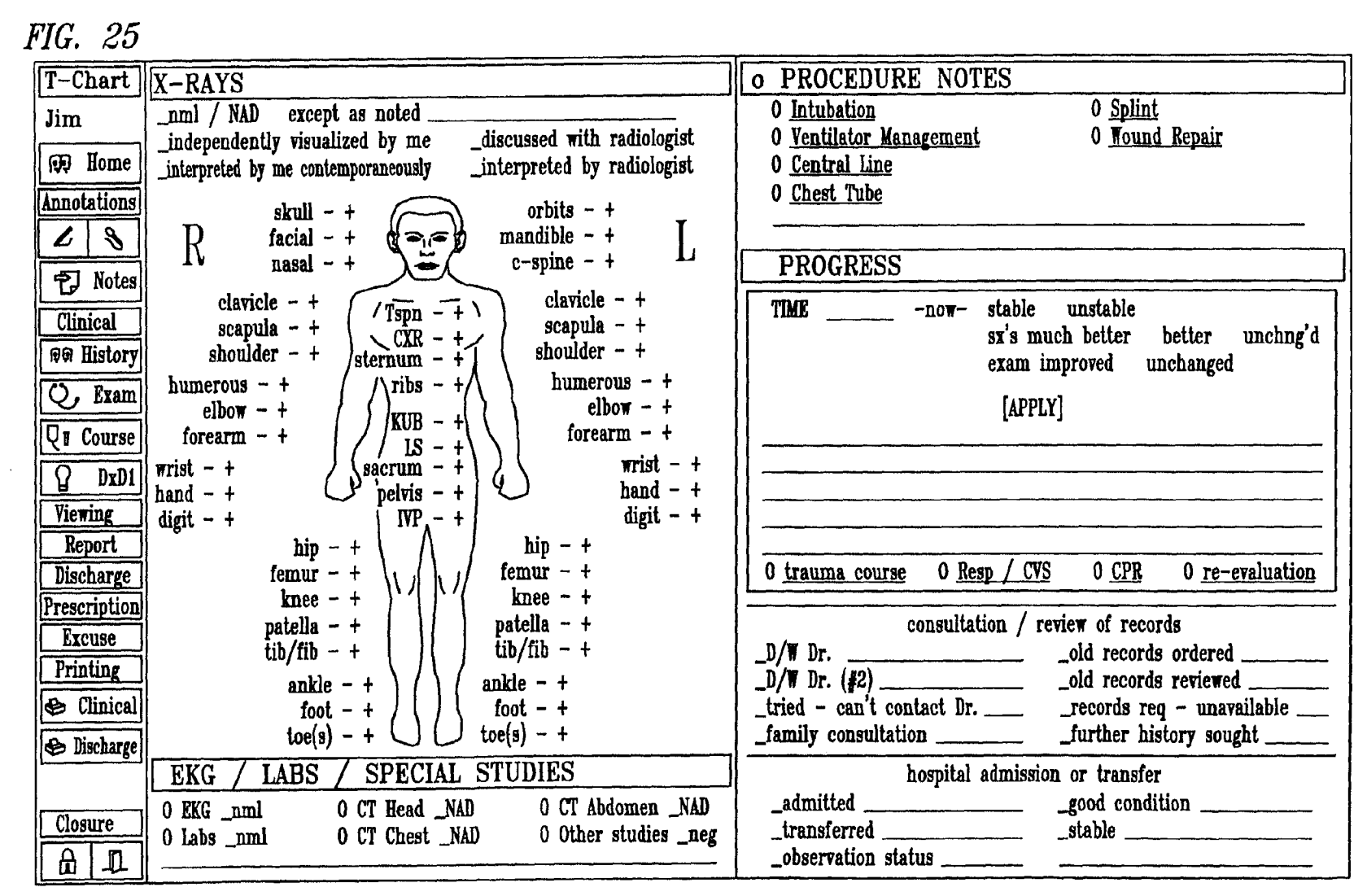

In FIG. 23-26, a set of template sheets is shown illustrating the differences between the "History", "Exam", "Course", and "DxDI" sheets. All of these templates are for a motor vehicle accident, with FIG. 23 showing a sheet for "History," FIG. 24 shows the "Exam" sheet, FIG. 25 shows a sheet for "Course," and FIG. 26 shows a sheet for "DxDI." These sheets as discussed previously relate to different aspects of a patient's treatment. While not discussed above, the templates may also include sub-templates, which permit the entry of additional data about any particular heading shown on the template. Various findings in the sub-templates may also include modifiers, which include additional entries, which may be made with respect to any of the conditions referred to on the sub-template.

Figure 27:
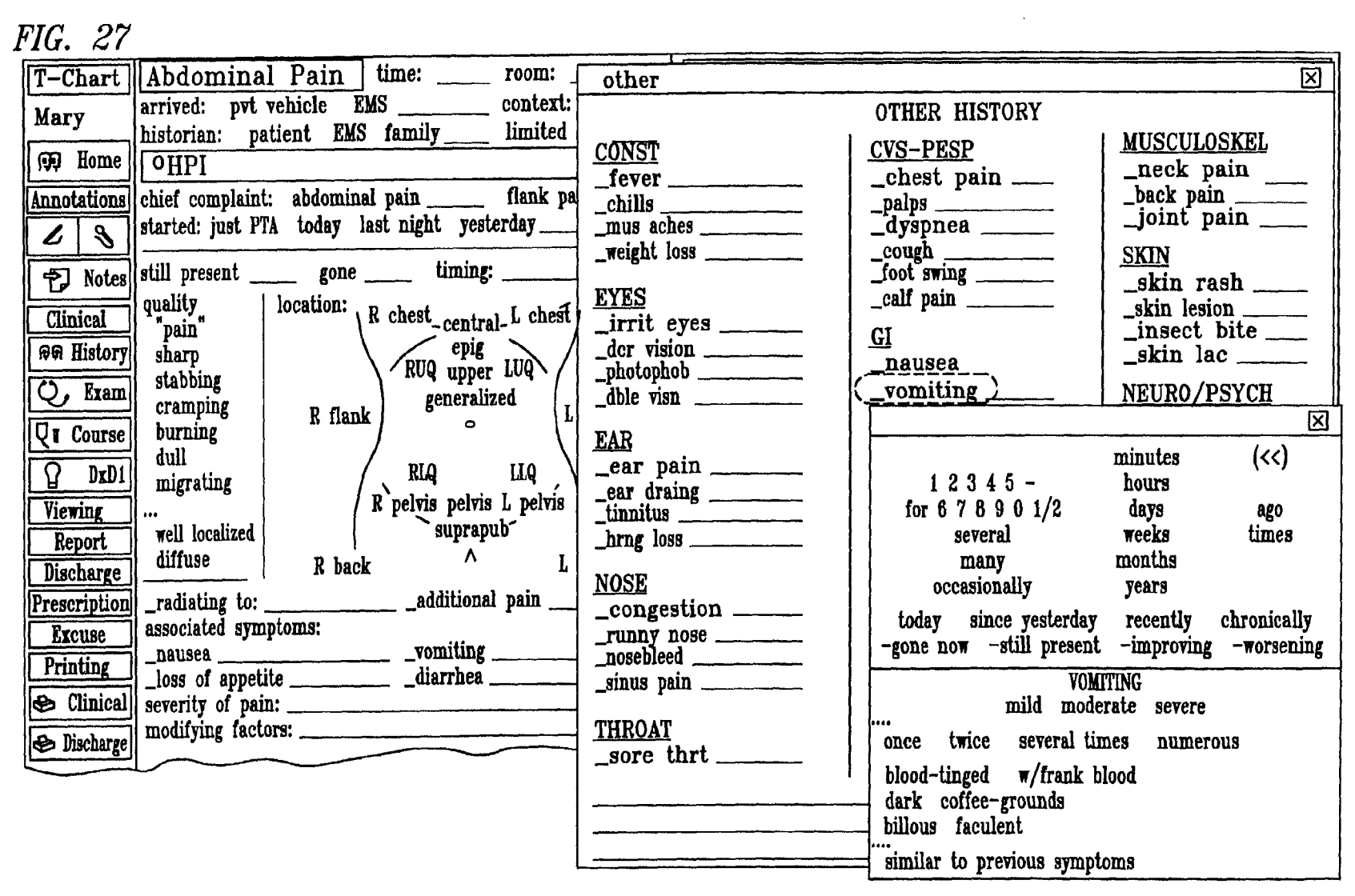

In FIG. 27, a sub-template is shown. The sub-template is headed "Other History." This sub-template is available by clicking on the circle in front of the heading "HPI." This sub-template enables the entry of additional information.

As further shown in FIG. 27, a modifier is available and is shown on the sub template in connection with vomiting. Additional information can be shown by marking entries on the modifier as discussed previously.

As shown, these screen displays demonstrate one embodiment of the system of the present invention for use in a hospital emergency room. As indicated, this system can be used for a wide variety of data entry applications. The system registers a positive finding when a tablet pen touches the left side of an unmarked finding. It should be appreciated that any number of systems can be used for data entry. Typically in the current system, a negative finding is registered when the user right clicks or taps the right side of an unmarked finding. The selection of a previously marked finding clears or reverses the indicated mark thereby providing the user with a intuitive mechanism for correcting data entry errors. Those discussed herein are preferred and have been found to be effective. They should be considered to be illustrative disclosures of methods for entering, reporting and distributing the data.

On tablet-based systems, in addition to recognizing the left and right taps as requests to enter positive and negative findings respectively, it is desirable for the software to recognize pen movements, circling or backslashing the word and to translate those into positive and negative findings. The effect observed by the user is that drawing a circle or a backslash around the typesetting enters the positive or negative findings. The circles and backslashes can be used to illustrate multiple positive or negative findings.

The forms are desirably laid out to permit the user to readily enter data with a minimum of effort. Accordingly, the forms should provide the ability to enter most data by yes/no entries.

In the present system, most of the templates are desirably designed so that a simple yes/no answer can be used to indicate the data. For example, "The patient has chest pain." or "The patient does not have chest pain." Sometimes it is desirable to provide more information. If specified by the form layout, the software must present a visual cue that entry of detailed findings is possible. One such visual cue is to draw a horizontal line to the right of the finding, as illustrated on all findings under EYES in the ROS section in FIG. 27. In such cases, the user can click or tap the horizontal line in order to request an opportunity to enter more detailed information about the finding in question. The software responds by presenting one or more of the following data entry options, as specified by the layout: (1) simple text, (2) sentence builders, and (3) modifiers. The user may enter data as desired, and then dismiss the data entry option(s), generally by either (a) clicking or tapping a "close" icon associated with the data entry option or (b) activating data entry into an unrelated finding by clicking or tapping it.

As illustrated previously, the software in the system should present a visual clue that detailed information has been entered for a given finding. For instance, as shown in FIG. 22 after the word "Cough" additional information is shown. This provides an indication that more information is available with respect to this finding.

It is not considered necessary that the visual clue for detailed findings actually shows the detailed findings completely. It is sufficient that the indication is made that detailed findings were recorded.

In addition for providing for the entry of data as a detailed finding, the software should also enter simple text (simple sentences) that stands on its own. This should be enterable using conventional methods such as the use of a backspace, left and right arrow and similar navigation keys, word wrap, use of scroll bars and the like to access the entire text and voice or handwriting recognition should be accepted. The entered text should then be displayed over the lines near the entries or at other places as indicated. If the entered text is too lengthy to appear within the available space a visual clue should be indicated.

The entry of detailed findings can be augmented with sentence builders to accelerate entry of simple text as shown in FIG. 27. The upper portion of the pull-down shown permits selection of for instance "for", "several" and "days". This would result in a report that, "The patient has vomiting (for several days)". Additional information can be shown by typing in the data entry space provided. Information may also be shown by selecting the findings on the modifier (pull-down). Sentence builders are another data entry option, which may be invoked in the form design.

This system may also be used with a medical records distribution system. Typically such medical record distribution systems comprise a computer programmed to access a database of such medical records and a database including distribution options. These options may include distribution of the information, for instance, to a second or additional physicians, to insurance companies, or other payers and the like. Normally, the distribution option is selectable for each medical record, which is to be distributed. The selected option may be implemented by electronically distributing the records via e-mail or other similar communication systems or the distribution system may produce a hard copy letter or the like, of the medical records to be distributed with suitable addresses for mailing to the desired recipients. Desirably, the system is also in communication with a database, which maintains a record of the distributed medical records and of the recipients of those medical records.

In FIG. 28, an exam template for abdominal pain is shown. On this template, various findings have been indicated positively by circles.

A clinical report is shown in FIG. 29 reporting the data entered in FIG. 28. In FIG. 28, by clicking on FEM GENITALIA a sub-template headed "Pelvic Exam" is available as shown in FIG. 30. Certain findings have been indicated on this sub-template as shown by circles.

In FIG. 31, a clinical report including this information, in addition to that available previously from FIG. 28, is shown.

By clicking on the line following the entry for "Time" under "Progress" in FIG. 32, a "Progress and Procedures Note" is available for indicating changes in the patient's condition, medicines administered and the like. In the note shown, the patient has been subjected to observation, tests have been returned, an analgesic has been administered and a narcotic has been administered. As a result of this treatment, the patient's condition is much better and the exam findings have improved. It will be noted that under the "Note" are notes from previous entries on previous "Notes." This allows the physician to enter patient treatment information sequentially. If it is desired to enter the time, it can be entered, but is not necessary. It is generally considered more important to enter the sequence of treatment rather than the exact times that the treatments are performed. In FIG. 33 the entered data is shown for the notes cumulatively in the "Progress" section.

In FIG. 34, the clinical report is provided. The "PAST HISTORY" includes data entered previously on a History template, the "PHYSICAL EXAM" information includes information previously entered on an Exam template and the "PROGRESS AND PROCEDURES" notes are entered on the Progress and Procedures section.

The reports of the recorded data are typically made by programming, which produces the reports as a plurality of simple sentences having a single object or a single clause.

Figure 35:
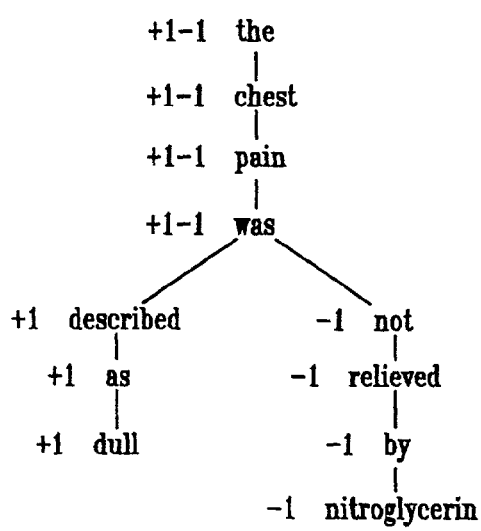

As shown in FIG. 35, two phrases are shown in a diagram for condensing these phrases. The phrases are "The chest pain was described as dull." and "The chest pain was not relieved by nitroglycerin." These two phrases have been drawn as a diagram which shows the essential content of an internal data structure created by the computer program upon processing those phrases. The preferred form of the internal data structure is generally a data tree, although other suitable structures known to those skilled in the art could be used.

The program builds the tree by processing each phrase in turn. Each successive word in each phrase is added to the tree so that the collective content of all the phrases is contained in the tree as suggested in FIG. 35.

The program also maintains a tally of the number of positive and negative phrases found for each word in the tree. As shown in FIG. 35, the first four words of all phrases in this example are "the", "chest", "pain" and "was, and each of these is associated with one positive phrase ("+1" in the diagram) and one negative phrase ("−1" in the diagram). As described below, the program may permit the author flexibility in the manner in which the program generates text from the tree thus produced. The information required for the program to accommodate the author's wishes, such as desired ordering of phrases or use of conjunctive words as described below, can be stored in the nodes of the tree. The particular information to be stored in each node depends upon the options desired.

To generate sentences from the tree, the program traverses the nodes of the tree, nominally in order of their appearance in the tree, but altered as necessary to reflect any desired ordering imperatives. Successive nodes such as "the", "chest", "pain" and "was" in FIG. 35 constitute a common pretext for any sentence(s) generated from the least significant, or rightmost, node, in this case "was". The traversal process at a node which branches into two or more subtrees, such as "was" in FIG. 35, produces the necessary sentence(s) as the common pretext, in this case "The chest pain was" followed by a list of phrases generated from each subtree, such that any positive phrases are extracted from the subtrees and combined in an "a, b, c and d" pattern, and similarly any negative phrases are extracted from the subtrees and combined in an "a, b, c or d" pattern, and such that if both negative and positive phrases were found, the positive phrases come first and are followed by the conjunctive word "but" and then the extracted negative phrases.

Accordingly, the sentence resulting from the combination of the phrases in FIG. 35 would say, "The chest pain was described as dull but not relieved by nitroglycerin." In the construction of the sentences, "but" is used to indicate a negative and in the event that more than one negative clause is used, the clauses may be separated by "or's." In the recitation of a plurality of positive phrases, the phrases are separated by "and's." Arbitrarily, it has been determined the sentences containing more than five clauses are unduly complex and the combination of single sentences is preferably limited to five clauses.

Figure 36:
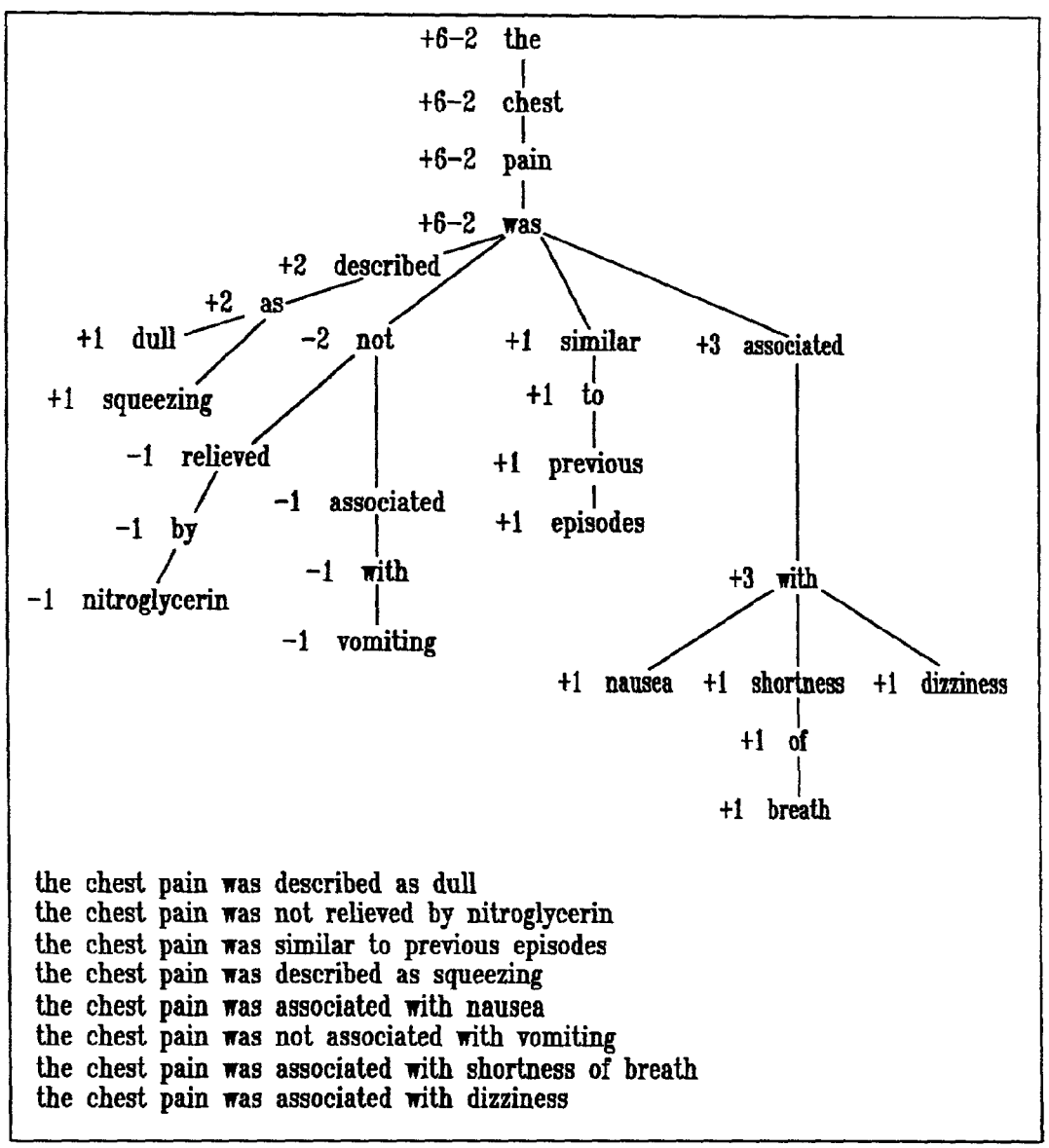

In FIG. 36, a more complicated diagram is shown. The eight sentences shown beneath the diagram are to be combined into more complex and more readable sentences. It will be noted that "the" appears in six positive statements and two negative statements. This assignment of values continues through the word "was." "Was" is followed by the word "described" twice, indicated by the numeral "+2" beside the word "described." The word "as" similarly appears twice and the words "dull" and "squeezing" each appear once. A similar assignment of numbers is found with the negative statements which are shown directly beneath "was" with a "−2" being assigned to "not" and "−1's" being assigned to the words following the "not." Similarly, the word "similar" occurs once and this is shown by the "+1's". The word "associated" follows the word "was" three times and this is indicated by the numerals "+3" with each of the individual phrases following from the word "associated" being numbered with "+1's". The net result of the combination is that it is not possible to combine all of the clauses without exceeding the limitation of five clauses per sentence.

The traversal process described above works well even when a tree contains complex nested subtrees such as that shown in FIG. 36. In such a case, the subtrees are traversed as before and the resulting text still reads well. New sentences can be started at any given node, whenever necessary either to avoid exceeding the maximum number of clauses, or to comply with the author's requirements. Accordingly, while a number of combinations might be possible, the most likely combination is the following. "The chest pain was described as dull and squeezing and similar to previous episodes but not relieved by nitroglycerin or associated with vomiting. The chest pain was associated with nausea, shortness of breath and dizziness."

Similar applications can be made to any group of sentences produced by the program, which produces simple sentences having a single object or clause. Clearly, the assignment of a limit of five clauses per sentence is arbitrary and fewer or more clauses could be used if desired. While this embodiment is relatively specific, it should be understood that a large number of programs using this type of approach could be used to convert the simple sentences to longer sentences to more accurately and readably convey the data.

In addition to the limitations discussed above, the program is designed to permit the author flexibility in the expression. For instance, in the combination of the two sentences referred to in FIG. 35, the resulting sentence could also by produced by an option which causes the sentence to read "The chest pain was described as dull, but was not relieved by nitroglycerin." Clearly the use of the second occurrence of the word "was" is optional and may be preferred by some users. Further, the program offers the capability to select a conjunction of choice. For instance, "and", "or" or "nor" could be selected. The appropriate conjunctive is selectable by the user. The program will provide conjunctives as indicated previously with "and" separating positive clauses and "or" separating negative clauses with a "but" separating the positive and negative clauses, unless modified.

The program also permits the user to alter the order of the clauses by assigning selected number values to the clauses to designate the order in which they appear in the sentence. The simple sentences may be grouped as desired in the combined sentence by designating the clauses in the order in which they are to appear in the combined sentence by assigning numbers to each of the clauses. As a further feature, selected words may be left in the combined sentence which would otherwise have been deleted by bracketing or indicating the words which are to be retained which would normally have been deleted.

It may be desirable in some instances to eliminate redundancy and in other areas to create deliberate redundancy. In general, considerable flexibility is left to the user of the program to generate the combined sentence to most accurately reflect the combined meaning of the simple sentences.

Many variations and modifications are possible within the scope of this technique. In general, special punctuation may be used as an instruction to the program to add words, delete words, reorganize words and the like. Further, the desired punctuation to arrange the clauses in a desired order may be specified on the template or sub-template or modifier sheets so that when the simple sentences are produced, they are produced with the desired indicators to cause the combined sentence to be produced in a desired form. Other variations may also appear desirable to those skilled in the art based upon the foregoing description.

Further with reference to FIG. 34, please note that the clinical report is organized to recite the name of the template from which the data is obtained. In the case of the physical exam, it is laid out to refer to the section of the physical exam from which the data is entered. for instance, the data is entered for: "Eyes", "ENT", "Neck", "Abdomen", "GU", "Skin", and "Neuro." In the Progress and Procedures section, the data reported is all reported under the ED Course, which is the section in which the evaluation and reassessment data is reported.

Figure 37:
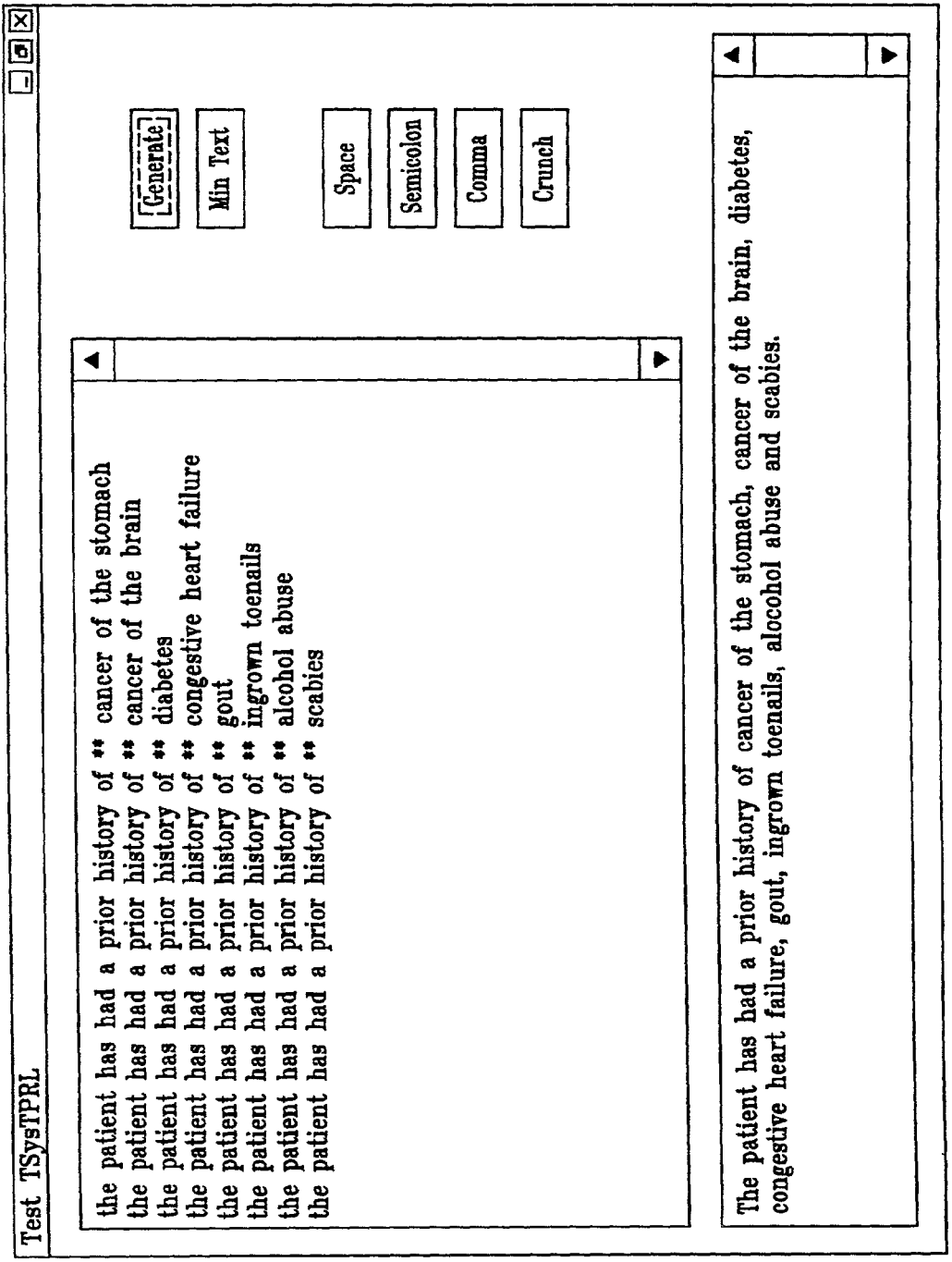

In FIG. 37, a plurality of sentences is shown with an indication ahead of each clause indicating that there is to be no clause reduction. This embodiment may be desirable in many instances with a prior medical history where it is desired that the phrases be made available to the physician without modification.

In further modifications, for instance with the vomiting modifiers discussed above, it may be indicated that severe vomiting is present, that the vomit is blood tinged and contains frank blood. This sentence may be varied by suitable punctuation to read "He has had severe blood tinged vomiting containing frank blood." or alternatively could be punctuated to read "He has had severe blood tinged vomiting. The vomitus contains frank blood." (FIG. 27) The development of punctuation to position the clauses relative to each other and the punctuation available to remove redundancy and to properly place adjectives and the like permits tremendous flexibility in the construction of the complex sentences.

In summary, the present system is effective to record medical data or other data which is conveniently entered by a professional or other observer by entering yes/no entries into a system to enter the data effectively, transmit it to a desired records system or otherwise make it available for use with respect to the individual, reported by the recorder or by another party.

While the description above has illustrated the invention specifically with respect to a medical emergency room data entry system, it should be understood that this system is much more widely usable in other applications although the use of the system is particularly effective for the entry of data in a medical emergency room situation.

Having thus described the invention by reference to certain of its preferred embodiments, it is noted that the embodiments described are illustrative rather than limiting in nature and that many variations and modifications are possible within the scope of the present invention. Many such variations and modifications may be considered to be obvious or desirable to those skilled in the art based upon the foregoing description of preferred embodiments.

Having thus described the invention, we claim:

1. A computer program product for facilitating an emergency room medical professional/patient encounter workflow, the computer program product including a computer-readable medium having instructions stored thereon, which when executed the computing device is configured to:
receive a selection of a chief medical complaint for a patient, wherein the selection of a chief medical complaint generates a selection of a template based on that specifically selected chief medical complaint;
present a plurality of screen presentations of the template to a medical professional, wherein the plurality of screen presentations includes multiple screens having selectable clinical items which are pre-identified to be of particular concern to the selected chief medical complaint,
wherein a first screen in the multiple screens having selectable clinical items which are pre-identified to be of particular concern to the selected chief medical complaint is configured for a first clinical phase of the medical professional/patient encounter,
wherein a second screen in the multiple screens having selectable clinical items which are pre-identified to be of particular concern to the selected chief medical complaint is configured for a second clinical phase of the medical professional/patient encounter,
wherein at least one selectable clinical item in the selectable clinical items includes a textual representation of the selectable clinical item, the textual representation being the actual textual label representing the selectable clinical item; and
receive yes/no data entries for the selectable clinical items, wherein the yes/no data entries are entered primarily without the use of conventional check boxes/radio buttons, wherein a first type of yes/no data entry indicates a positive finding, and a second type of yes/no data entry indicates a negative finding,
wherein a selection of a positive finding of the at least one selectable clinical item and a selection of the negative finding of the at least one selectable clinical item require an affirmative selection from the medical professional,
wherein the selection of the positive finding of the at least one selectable clinical item is performed on the textual representation of the at least one selectable clinical item, and the selection of the negative finding of the at least one selectable clinical item is performed on the textual representation of the at least one selectable clinical item,
wherein the selection of the positive finding of the at least one selectable clinical item causes a first visual indicator to be displayed on the textual representation of the at least one selectable clinical item, and the selection of the negative finding of the at least one selectable clinical item causes a second visual indicator to be displayed on the textual representation of the at least one selectable clinical item, the first visual indicator being different than the second visual indicator.

2. The computing device of claim 1 wherein the selectable clinical items are words representing a symptom which corresponds to the selected chief medical complaint.

3. The computing device of claim 1, wherein the computing device is further configured to capture additional medical information regarding at least one selectable clinical item.

4. The computing device of claim 3 wherein the computing device is further configured to display a visual cue that additional medical information regarding at least one selectable clinical item may be entered.

5. The computing device of claim 4 wherein the computing device is further configured to display an additional menu when the visual cue is selected, the additional menu including additional selectable clinical items of particular concern to the selected clinical item.

6. The computing device of claim 5 wherein the computing device is further configured to receive yes/no data entries for the selectable clinical items of the additional menu, wherein the yes/no data entries are entered primarily without the use of conventional check boxes/radio buttons.

7. The computing device of claim 1 wherein the computing device is further configured to display a pre-identified graphic of an anatomical area on at least one of the plurality of screen presentations, wherein the pre-identified graphic shows only areas of concern for the selected chief medical complaint.

8. The computing device of claim 7 wherein the pre-identified graphic comprises selectable clinical item labels overlaid on the graphic.

9. The computing device of claim 1 wherein the computing device is further configured to receive a primary user input of the at least one selectable clinical item to indicate the selection of the positive finding of the at least one selectable clinical item and a secondary user input of the at least one selectable clinical item to indicate the selection of the negative finding of the at least one selectable clinical item.

10. The computing device of claim 9 wherein the primary user input is a left mouse click on the clinical item and the secondary user input is a right mouse click on the clinical item.

11. The computing device of claim 9 wherein the primary user input is indicated by tapping one side of the clinical item and the secondary user input is indicated by tapping another side of the clinical item.

12. The computing device of claim 9 wherein the displayed first visual indicator is a circle encircling the selected clinical item and the displayed second visual indicator is a strikethrough of the selected clinical item.

13. The computing device of claim 1 wherein the computing device is further configured to compile a textual prose representation correlating data from selected clinical items as each item is selected.

14. A method comprising:
presenting to a user a listing of chief medical complaints on a computer display;
upon receiving a selection of a chief medical complaint for a patient at a computing device, presenting a plurality of screen presentations to a medical professional, wherein the plurality of screen presentations include multiple screens having selectable clinical items which are pre-identified to be of particular concern to the selected chief medical complaint,
wherein a first screen in the multiple screens having selectable clinical items which are pre-identified to be of particular concern to the selected chief medical complaint is configured for a first clinical phase of the medical professional/patient encounter,
wherein a second screen in the multiple screens having selectable clinical items which are pre-identified to be of particular concern to the selected chief medical complaint is configured for a second clinical phase of the medical professional/patient encounter,
wherein at least one selectable clinical item in the selectable clinical items includes a textual representation of the selectable clinical item, the textual representation being the actual textual label representing the selectable clinical item; and receiving yes/no data entries for the selectable clinical items at the computing device, wherein the yes/no data entries are entered primarily without the use of conventional check boxes/radio buttons, wherein a first type of yes/no data entry indicates a positive finding, and a second type of yes/no data entry indicates a negative finding, wherein a selection of a positive finding of the at least one selectable clinical item and a selection of a negative finding of the at least one selectable clinical item require an affirmative selection from the medical professional, wherein the selection of the positive finding of the at least one selectable clinical item is performed on the textual representation of the at least one selectable clinical item, and the selection of the negative finding of the of the at least one selectable clinical item is performed on the textual representation of the of the at least one selectable clinical item, wherein the selection of the positive finding of the at least one selectable clinical item causes a first visual indicator to be displayed on the textual representation of the at least one selectable clinical item, and the selection of the negative finding of the at least one selectable clinical item causes a second visual indicator to be displayed on the textual representation of the at least one selectable clinical item, the first visual indicator being different than the second visual indicator.

15. The method of claim 14, further comprising:

displaying a visual cue indicating that additional medical information regarding at least one selectable clinical item may be entered; and receiving additional medical information regarding at least one selectable clinical item.

16. The method of claim 15 further comprising:

displaying an additional menu when the visual cue is selected, the additional menu including additional selectable clinical items of particular concern to the selected clinical item; and receiving yes/no data entries for the selectable clinical items of the additional menu, wherein the yes/no data entries are entered primarily without the use of conventional check boxes/radio buttons.

17. The method of claim 14 further comprising:

presenting to a user a pre-identified graphic of an anatomical area on at least one of the plurality of screen presentations, wherein the pre-identified graphic shows only areas of concern associated with the selected chief medical complaint.

18. The method of claim 17 wherein the pre-identified graphic comprises selectable clinical item labels overlaid on the graphic.

19. The method of claim 14 further comprising receiving a primary user input for the at least one selectable clinical items to indicate the selection of the positive finding of the at least one selectable clinical item and a secondary user input for the at least one selectable clinical item to indicate the selection of the negative finding of the at least one selectable clinical item.

20. The method of claim 19 wherein the primary user input is a left mouse click on the clinical item and the secondary user input is a right mouse click on the clinical item.

21. The method of claim 19 wherein the primary user input is indicated by tapping one side of the clinical item and the secondary user input is indicated by tapping another side of the clinical item.

22. The method of claim 19 wherein the displayed first visual indicator is a circle encircling the selected clinical item and the displayed second visual indicator is a strike-through of the selected clinical item.

23. The method of claim 14 further comprising compiling a textual prose representation correlating data from selected clinical items as each item is selected.

* * * * *